(12) United States Patent
Mikaelian et al.

(10) Patent No.: US 12,403,338 B2
(45) Date of Patent: Sep. 2, 2025

(54) FILTERING FACEPIECE RESPIRATOR WITH AN ADJUSTABLE INHALATION-EXHALATION VALVE

(71) Applicants: Andrew J. Mikaelian, Westlake Village, CA (US); Nyree S. Masoian, San Ramon, CA (US); Danielle K. Mikaelian, Westlake Village, CA (US)

(72) Inventors: Andrew J. Mikaelian, Westlake Village, CA (US); Nyree S. Masoian, San Ramon, CA (US); Danielle K. Mikaelian, Westlake Village, CA (US)

( * ) Notice: Subject to any disclaimer, the term of this patent is extended or adjusted under 35 U.S.C. 154(b) by 861 days.

(21) Appl. No.: 17/462,351

(22) Filed: Aug. 31, 2021

(65) Prior Publication Data

US 2022/0088423 A1    Mar. 24, 2022

Related U.S. Application Data

(60) Provisional application No. 63/082,443, filed on Sep. 23, 2020.

(51) Int. Cl.
*A62B 18/10*       (2006.01)
*A41D 13/11*       (2006.01)
(Continued)

(52) U.S. Cl.
CPC ............ *A62B 18/10* (2013.01); *A41D 13/11* (2013.01); *A61M 16/202* (2014.02); *A62B 9/006* (2013.01);
(Continued)

(58) Field of Classification Search
CPC ..... A62B 18/10; A62B 23/025; A62B 18/086; A62B 27/00; F16K 15/148; F16K 15/1825; A63B 23/18
See application file for complete search history.

(56) References Cited

U.S. PATENT DOCUMENTS 9,579,540 B1 *   2/2017   Danford ............ A63B 21/0085
2002/0023651 A1 *   2/2002   Japuntich ............... A41D 13/11
128/206.15

(Continued)

FOREIGN PATENT DOCUMENTS

CN        108472519 A  *  8/2018   ............. A62B 18/10

OTHER PUBLICATIONS

CN 108472519 Machine translation (Year: 2018).*

*Primary Examiner* — Victoria Murphy
*Assistant Examiner* — Sara K Toich
(74) *Attorney, Agent, or Firm* — ONE LLP

(57) ABSTRACT

A filtering facepiece respirator is provided. The filtering facepiece respirator includes a facemask adapted to fit over the nose and mouth of a wearer, where the facemask comprises a mask body containing a filtering structure. A harness is coupled to the mask body for securing the facemask on the face of the wearer, and a mechanical valve is coupled to a portion of the mask body proximate the wearer's mouth. The valve may be adjusted between a first mode of operation and a second mode of operation, where in the first mode of operation is permitted to flow through the valve on exhalation but not on inhalation and in the second mode of operation air is obstructed from flowing through the valve on exhalation and inhalation. There is an optional third mode of operation where air is permitted to flow through the valve on inhalation and exhalation.

10 Claims, 13 Drawing Sheets

(51) Int. Cl.

| | |
|---|---|
| *A61M 16/20* | (2006.01) |
| *A62B 9/00* | (2006.01) |
| *A62B 18/08* | (2006.01) |
| *A62B 23/02* | (2006.01) |
| *F16K 15/14* | (2006.01) |
| *F16K 15/18* | (2006.01) |
| *H04Q 9/00* | (2006.01) |

(52) U.S. Cl.
CPC .......... *A62B 18/084* (2013.01); *A62B 23/025* (2013.01); *F16K 15/148* (2013.01); *F16K 15/1825* (2021.08); *H04Q 9/00* (2013.01); *H04Q 2209/40* (2013.01)

(56) References Cited

U.S. PATENT DOCUMENTS

| | | | | |
|---|---|---|---|---|
| 2018/0296876 | A1* | 10/2018 | Wenger | A63B 23/18 |
| 2020/0061399 | A1* | 2/2020 | Wade | A62B 18/025 |
| 2021/0370105 | A1* | 12/2021 | Chen | A62B 23/02 |

* cited by examiner

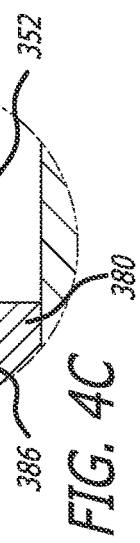
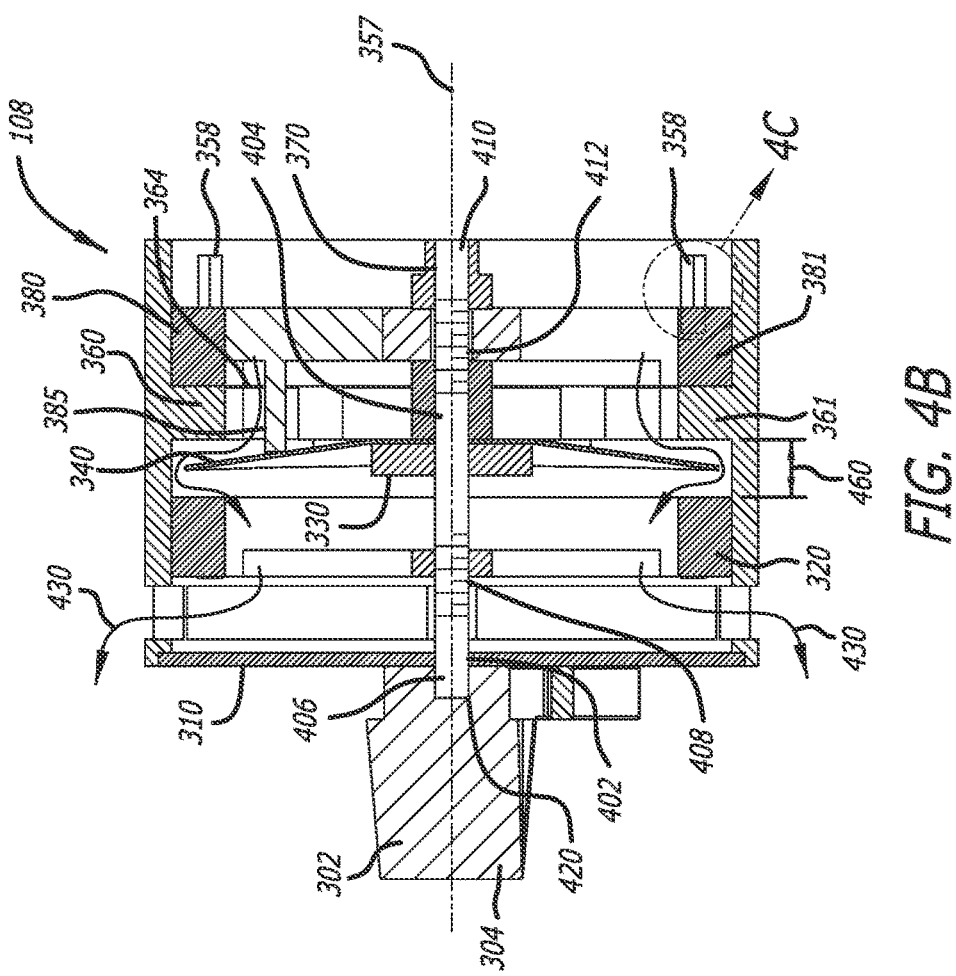
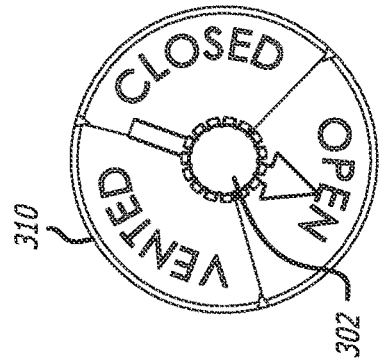

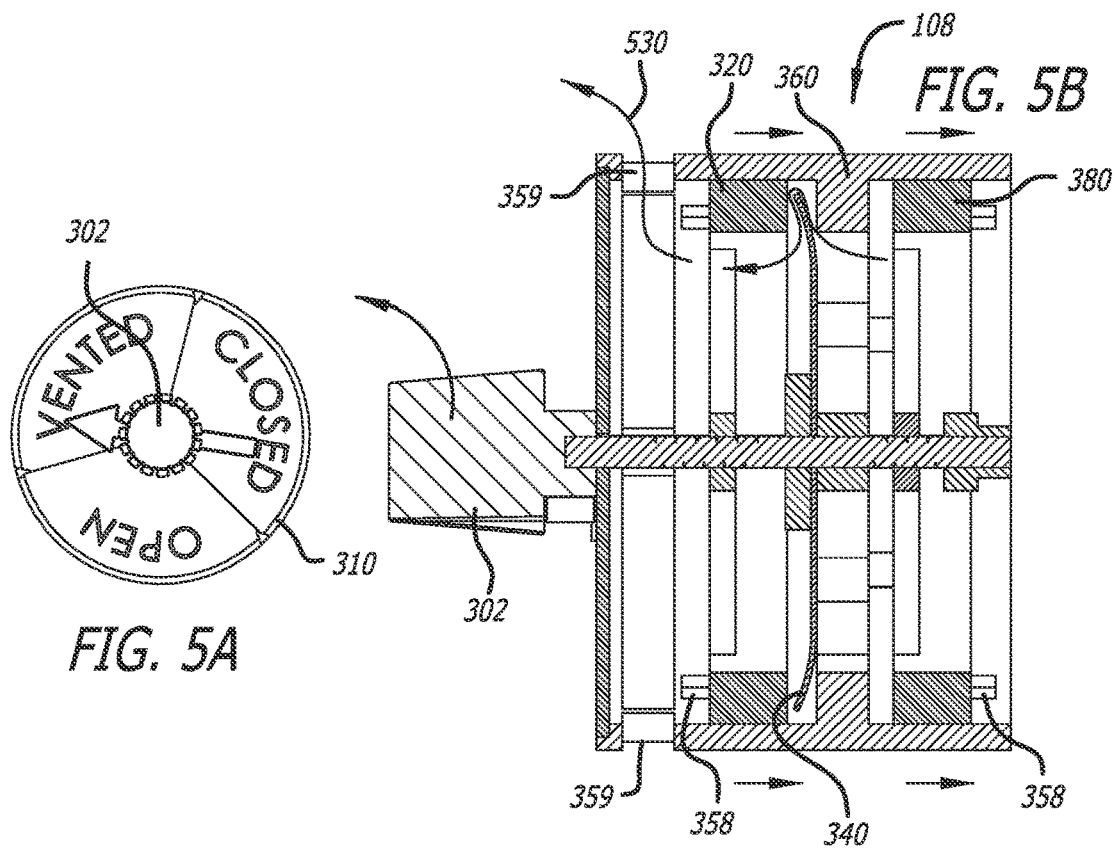
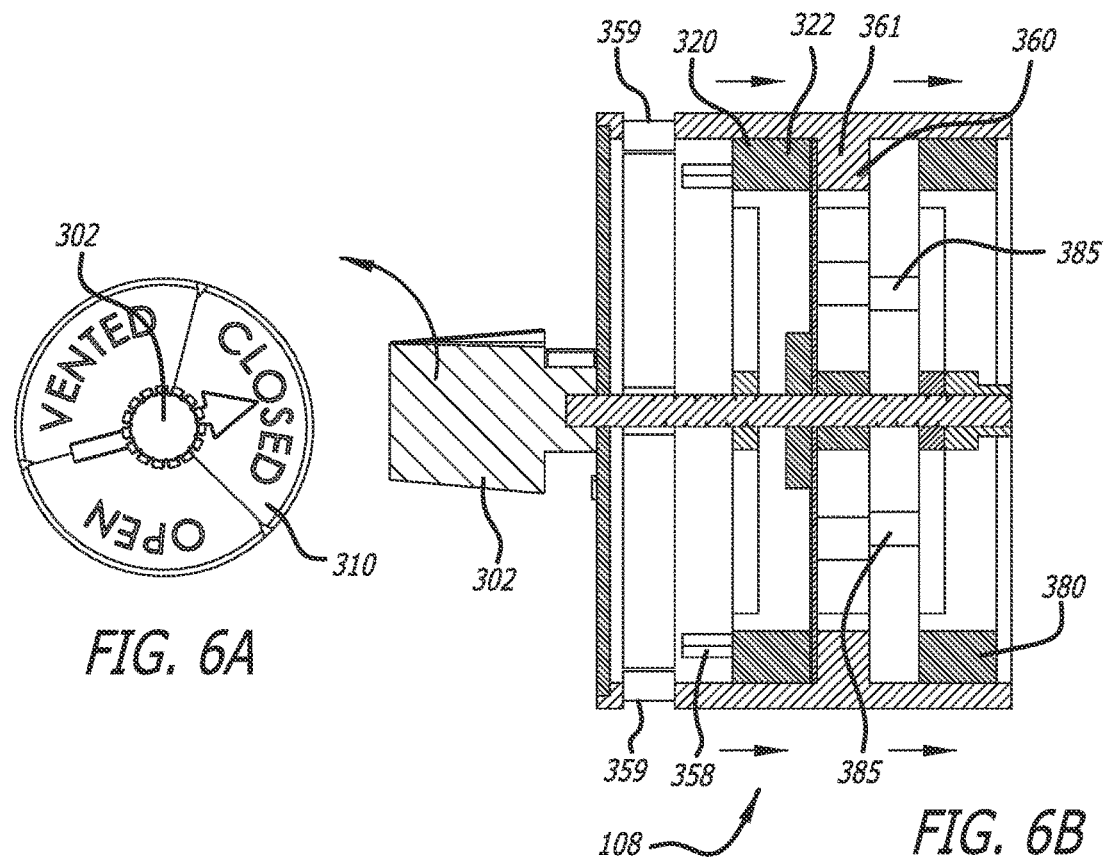

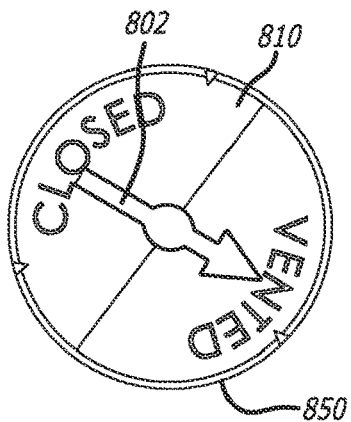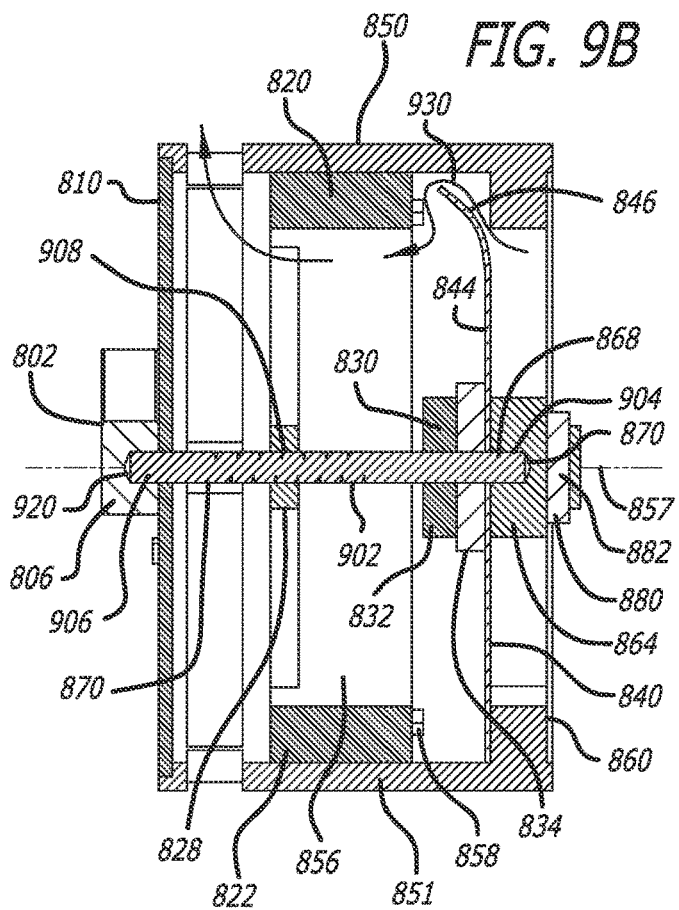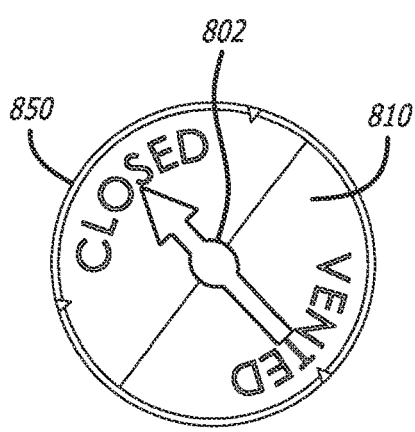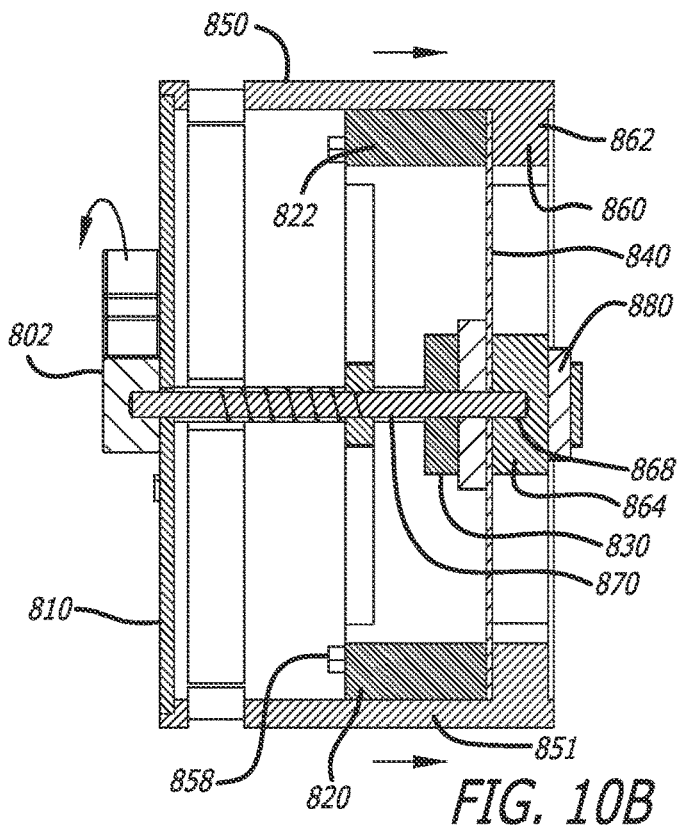

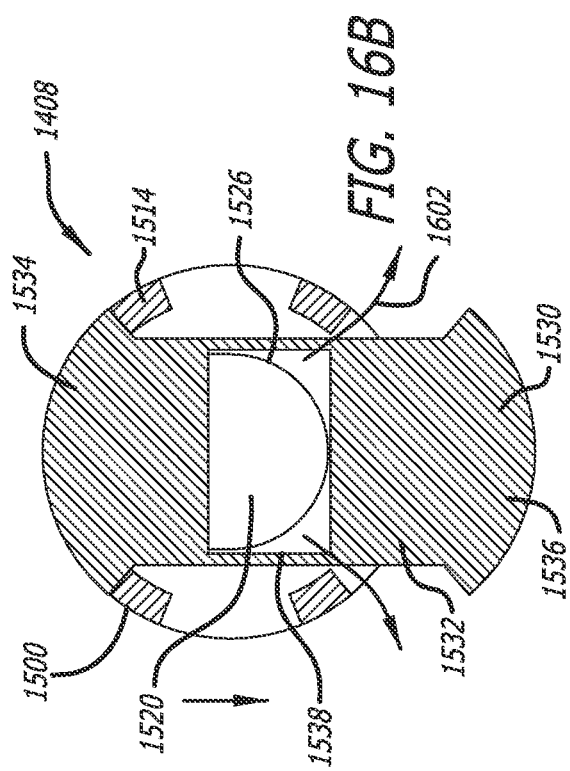
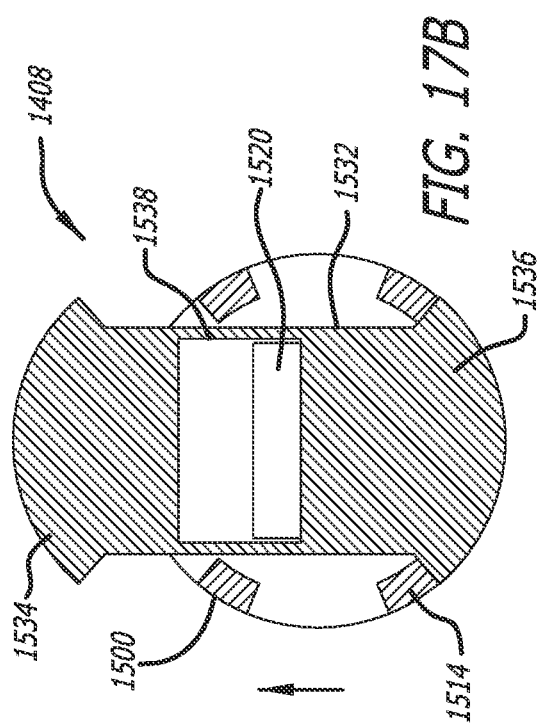
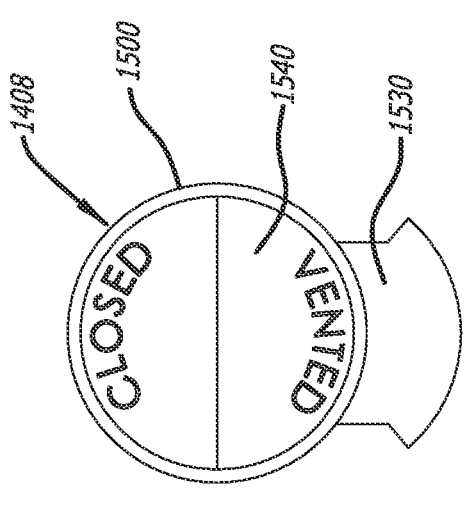
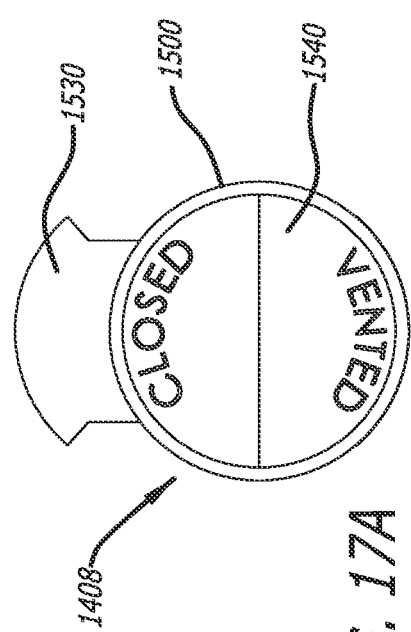

FILTERING FACEPIECE RESPIRATOR WITH AN ADJUSTABLE INHALATION-EXHALATION VALVE

CROSS-REFERENCE TO RELATED APPLICATION

The present application claims priority under 35 USC § 119(e) to U.S. Provisional Patent Application No. 63/082,443, filed on Sep. 23, 2020, titled FILTERING FACEPIECE RESPIRATOR WITH AN ADJUSTABLE INHALATION-EXHALATION VALVE, the disclosure of which is hereby incorporated by reference in its entirety for all purposes.

TECHNICAL FIELD

The present disclosure generally relates to personal protective equipment, and more specifically, to a filtering facepiece respirator that uses an adjustable inhalation-exhalation valve that is integrated into the mask body.

BACKGROUND

Filtering facepiece respirators are commonly worn over the mouth and nose of a person to prevent the individual from inhaling and/or exhaling microscopic particles, including infectious and non-infectious contaminants. The use of these devices has become much more common due to the recent SARS-CoV-2 (COVID-19) pandemic.

Conventional filtering facepiece respirators have either no valve or a valve that filters on inhalation but not on exhalation. These masks typically use a fine mesh of nonwoven polypropylene fabric for filtration. Wearing a non-valved respirator can trap exhaled air with a lower oxygen concentration and a higher carbon dioxide level than room air. This trapped air is then repeatedly rebreathed, causing hypoxemia and hypercapnia. The resulting acute symptoms of these alterations in oxygen and carbon dioxide include dizziness and headaches, causing a reduction in work efficiency and can negatively affect decision making. Chronic hypoxemia and hypercapnia can exacerbate pre-existing cardiac, pulmonary, vascular, neurologic, and metabolic conditions.

Prior to the COVID-19 pandemic, over 3 million United States employees in approximately 1.3 million workplaces were required to wear some kind of respiratory protection. Since early 2020, this number has increased greatly. An N95 filtering facepiece respirator (FFR) is a type of respirator which removes particles from the air that are breathed through it. These respirators filter out at least 95% of very small (0.3 microns) particles. Other respirator filter classes include N99, N100, R95, R99, R100, P95, P99, and P100. N95 FFRs are capable of filtering out all types of particles, including bacteria and viruses. The vast majority of these respirators do not have an expiratory valve. An N95 respirator with an exhalation valve provides a similar level of protection to the wearer as one that does not have a valve. The presence of an exhalation valve reduces exhalation resistance, which makes it easier to breathe on exhalation. A respirator with an exhalation valve keeps the face cooler, reduces moisture build-up inside the facepiece, and does not trap exhaled air as readily as a non-vented respirator. However, respirators with exhalation valves should not be used in many situations. Examples include but are not limited to times where a sterile field must be maintained (e.g., during an invasive procedure in a surgical suite) or when in close proximity to another individual when sick or during a pandemic (e.g., when working in a meatpacking plant or visiting a hospital during a pandemic or when sick) because the exhalation valve may allow unfiltered contaminated exhaled air to escape. If one only has a respirator with an exhalation valve but requires filtration on exhalation, the valve can be covered with another mask (surgical or procedure mask) that does not interfere with the respirator fit. This approach, however, wastes personal protective equipment. The mask design described in this invention would not require the placement of a second mask. The user would change the setting on the switch or have it changed remotely to close the exhalation valve.

The Occupational Safety and Health Administration (OSHA) requires an annual fit test to confirm the fit of any respirator that forms a tight seal on the wearer's face before it is used in the workplace. Once a fit test has been done to determine the best respirator model and size for a particular user, a user seal check should be done every time the respirator is to be worn to ensure an adequate seal is achieved. Presently, medical and nonmedical users of these non-vented masks have to physically remove them to inhale fresh air. A major issue arises in medical settings when healthcare providers remove a mask that is contaminated. It is not uncommon for these individuals to remove their masks numerous times per day, and this can lead to the transmission of a pathogen to the mask user or another individual. Each and every time the respirator is removed, another user seal check must be performed. Adding an adjustable valve that will allow the free flow of air out or in and out of the mask will circumvent the need for removal to clear trapped air or get a breath of fresh air and reverse hypoxia and hypercapnia. This increases safety by decreasing the chance of transferring infectious pathogens and adds to work efficiency by omitting repeated user seal checks.

A need therefore exists for a filtering facepiece respirator that addresses the aforestated challenges yet is easy to operate in various modes of operations depending on the wearer's desired need.

SUMMARY OF THE INVENTION

A manually operable filtering facepiece respirator is described herein. The filtering facepiece respirator includes a facemask adapted to fit over the nose and mouth of a wearer, where the facemask comprises a mask body containing a filtering structure. A harness is coupled to the mask body for securing the facemask on the face of the wearer, and a mechanical valve is coupled to a portion of the mask body proximate the wearer's mouth. The valve may be manually adjusted between a first mode of operation and a second mode of operation, where in the first mode of operation air is permitted to flow through the valve on exhalation but not on inhalation (vented mode), and in the second mode of operation air is obstructed from flowing through the valve on exhalation and inhalation (closed mode). In some embodiments, the valve can operate in a third mode where air is permitted to flow through the valve when the wearer inhales or exhales (open mode).

In some embodiments, the mask body comprises a first porous layer and a filtering layer. In other embodiments, the mask body comprises a first porous layer, a second porous layer, and a filtering layer, where the filtering layer is disposed between the first porous layer and the second porous layer.

The mechanical valve comprises a valve housing having an interior chamber, a fixed hub member disposed within the chamber, a first movable hub member disposed within the chamber, a pliable diaphragm disposed between the fixed hub member and the first movable hub member, a screw member disposed within the chamber extending along a longitudinal axis of the valve housing, and an adjustable dial. The adjustable dial is rotatable about the longitudinal axis, where the adjustable dial is coupled to the screw member and the screw member is threadedly coupled to the first movable hub member such that when the adjustable dial is rotated by the wearer, the screw member is also rotated and the threaded engagement between the screw member and the first movable hub member causes the first movable hub member to translate axially along the longitudinal axis away from or towards the fixed hub member.

In the first mode of operation, the first movable hub member is spaced apart from the fixed hub member, thus permitting an outer periphery of the diaphragm to be urged away from the fixed hub member under positive pressure, and air is allowed to freely flow through the valve when the wearer exhales. However, the outer periphery of the diaphragm is drawn towards the fixed hub member under negative pressure to obstruct the flow of air through the valve when the wearer inhales.

In the second mode of operation, the first movable hub member abuts the fixed hub member to secure the diaphragm therebetween. This retains an outer periphery of the diaphragm in contact with the fixed hub member to create a seal therebetween that obstructs air from flowing through the valve when the wearer exhales or inhales.

In some embodiments, the valve may operate in a third mode of operation. In this mode, air is permitted to flow through the valve when the wearer inhales or exhales.

The valve may be adjusted from one mode of operation to another mode of operation by a switch, slide, rod, rotating arm, lever, button, toggle, dial, knob, joystick, rheostat, or electronic controller.

The filtering facepiece respirator may further include a valve cap indicator coupled to a front portion of the valve housing. The valve cap indicator comprises a plate of material inscribed with indicia indicating the state of airflow through the valve utilizing a colored indicator, label, light indicator, or display. In some embodiments, the valve cap indicator may include an auditory system, such as a transistor, to broadcast the mode of operation to the wearer.

An automated filtering facepiece respirator is further described herein. The filtering facepiece respirator includes a facemask adapted to fit over the nose and mouth of a wearer, where the facemask comprises a mask body containing a filtering structure. A harness is coupled to the mask body for securing the facemask on the face of the wearer. A mechanical valve is coupled to a portion of the mask body proximate the wearer's mouth. The valve comprises a valve housing having a hollowed interior, a battery coupled to the housing, and a controller disposed within the hollowed interior. The controller is electrically coupled to the battery, where the controller adjusts the valve between a first mode of operation and a second mode of operation, where in the first mode of operation air is permitted to flow through the valve on exhalation but not on inhalation (vented) and in the second mode of operation air is restricted from flowing through the valve on inhalation and exhalation (closed).

In some embodiments, the mask body comprises a first porous layer and a filtering layer. In other embodiments, the mask body comprises a first porous layer, a second porous layer, and a filtering layer, where the filtering layer is disposed between the first porous layer and the second porous layer.

In this example, the valve comprises a valve housing having an interior chamber, a fixed hub member disposed within the chamber, a first movable hub member disposed within the chamber, a pliable diaphragm disposed between the fixed hub member and the first movable hub member, and a screw member disposed in the chamber extending along a longitudinal axis of the valve housing. The controller is in electrical communication with a motor coupled to the screw member to rotate the screw member. The screw member is threadedly coupled to the first movable hub member such that when the screw member is rotated by the motor, the threaded engagement between the screw member and the first movable hub member causes the first movable hub member to translate axially along the longitudinal axis away from or towards the fixed hub member.

In the first mode of operation, the first movable hub member is spaced apart from the fixed hub member, thus permitting an outer periphery of the diaphragm to be urged away from the fixed hub member under positive pressure and air is allowed to flow through the valve when the wearer exhales. But the outer periphery of the diaphragm is drawn towards the fixed hub member under negative pressure to obstruct the flow of air through the valve when the wearer inhales.

In the second mode of operation the, first movable hub member abuts the fixed hub member to secure the diaphragm therebetween, thus retaining an outer periphery of the diaphragm in contact with the fixed hub member to create a seal therebetween that obstruct air from flowing through the valve when the wearer exhales or inhales.

In some embodiments, the controller may be controlled by a mobile device via Bluetooth, WiFi, cellular, ultra-wideband, or RFID communications. In some embodiments, the controller may be integrated for use within public spaces such as offices, hospitals, clinics, restaurants, public and private buildings, service businesses, gyms and health clubs, and retailers.

In some embodiments, the filtering facepiece respirator may also include smart sensors that detect oxygen saturation levels, carbon dioxide levels, and volume of expired or inspired air. In these embodiments, the smart sensors may report data to a central monitoring unit, where the central monitoring unit uses the smart sensor data to alert the user of a change in mask environment conditions.

Other devices, apparatus, systems, methods, features, and advantages of the disclosure will be or will become apparent to one with skill in the art upon examination of the following figures and detailed description. It is intended that all such additional systems, methods, features, and advantages be included within this description, and be protected by the accompanying claims.

BRIEF DESCRIPTION OF THE FIGURES

The present invention may be better understood by referring to the following figures. Implementations of the invention are illustrated by way of example only and not limitation in the figures of the accompanying drawings. The components in the figures are not necessarily to scale, emphasis instead being placed upon illustrating the principles of the disclosure. In the figures, like reference numerals designate corresponding parts throughout the different views.

FIG. 4A a front view of the respiratory valve of FIG. 3 in an "open" mode of operation.

FIG. 4B is a cross-sectional view of the respiratory valve of FIG. 3 in an "open" mode of operation.

FIG. 4C is a partial close-up view of the elongated slot feature of the respiratory valve of FIG. 3.

FIG. 5A is a front view of the respiratory valve of FIG. 3 in a "vented" mode of operation.

FIG. 5B is a cross-sectional view of the respiratory valve of FIG. 3 in a "vented" mode of operation.

FIG. 6A is a front view of the respiratory valve of FIG. 3 in a "closed" mode of operation.

FIG. 6B is a cross-sectional view of the respiratory valve of FIG. 3 in a "closed" mode of operation.

FIG. 9A is a front view of the respiratory valve of FIG. 8 in a "vented" mode of operation.

FIG. 9B is a cross-sectional view of the respiratory valve of FIG. 8 in a "vented" mode of operation.

FIG. 10A is a front view of the respiratory valve of FIG. 8 in a "closed" mode of operation.

FIG. 10B is a cross-sectional view of the respiratory valve of FIG. 8 in a "closed" mode of operation.

FIG. 16A is a front view of the respiratory valve of FIG. 15 in a "vented" mode of operation.

FIG. 16B is a cross-sectional view of the respiratory valve of FIG. 15 in a "vented" mode of operation.

FIG. 17A is a front view of the respiratory valve of FIG. 15 in a "closed" mode of operation.

FIG. 17B is a cross-sectional view of the respiratory valve of FIG. 15 in a "closed" mode of operation.

DETAILED DESCRIPTION

FIGS. 1-17B illustrate examples of various embodiments of a filtering facepiece respirator. Generally, the filtering facepiece respirator includes a facemask adapted to fit over the nose and mouth of a wearer, where the facemask comprises a mask body containing a filtering structure. A harness is coupled to the mask body for securing the facemask on the face of the wearer, and a mechanical valve is coupled to a portion of the mask body proximate the wearer's mouth. The valve may be manually adjusted between a first mode of operation and a second mode of operation, where in the first mode of operation air is permitted to flow through the valve on exhalation but not on inhalation (vented mode) and in the second mode of operation air is obstructed from flowing through the valve on inhalation and exhalation (closed mode). In some implementations, the valve may be further adjusted to a third mode of operation, where in the third mode of operation air is permitted to flow through the valve when the wearer inhales and exhales (open mode)

Figure 1:
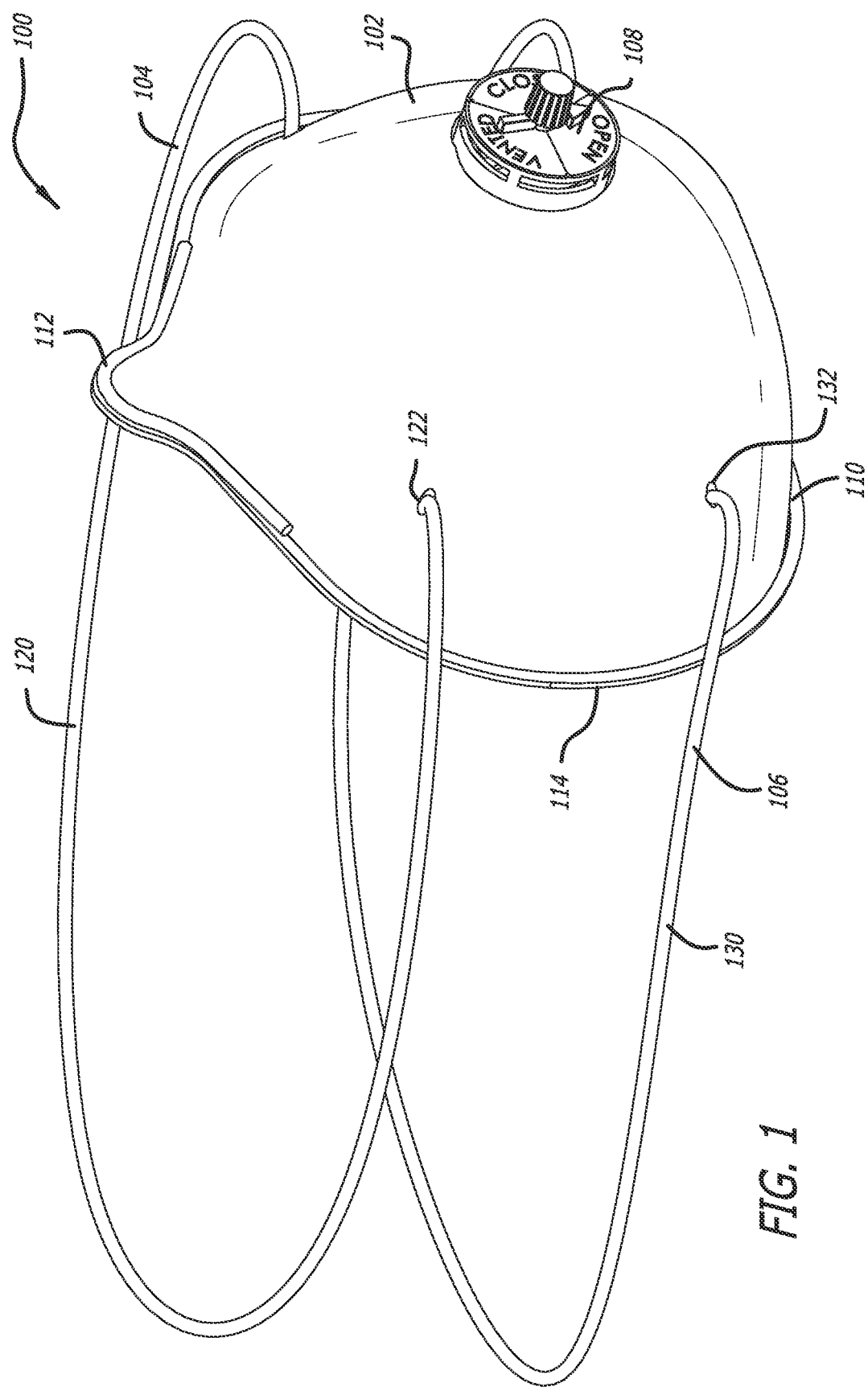
FIG. 1 is a perspective view of an example of a manual tri-mode filtering facepiece respirator in accordance with the teachings of the present disclosure.

FIG. 1 is a perspective view of one example embodiment of a manual tri-mode filtering facepiece respirator 100 according to the teaching of the present disclosure. As shown, the facepiece respirator 100 may include a facemask 102, an upper harness 104 coupled to an upper portion of the face mask 102, a lower harness 106 coupled to a lower portion of the facemask 102, and a respiratory valve 108 coupled to a central front portion of the facemask 102. In preferred implementations, the facemask 102 may include an outer contour 110 defined about a peripheral edge of the facemask 102 to substantially cover the nose and mouth of a wearer.

In most embodiments, the facemask 102 may further include a bendable reinforcement nosepiece 112 coupled to an upper portion of the outer contour 110. The nosepiece 112 may be coupled to the outer contour 110 of the facemask 102, for example, by glue, bonding, or other means at a portion of the facemask 102 fitting over the nose of the wearer. The nosepiece 112 may be constructed from a strip of aluminum, plastic, or any other pliable material. The nosepiece 112 is preferably flexible to allow the user to adjust the fit of the facemask 102 around the nose bridge area of the wearer. While the nosepiece 112 is shown affixed to the outside of the facemask 102, in other embodiments, the nosepiece 112 may be affixed to the outer contour 110 along the inside of the facemask 102 or embedded within the facemask 102 structure.

Figure 2:
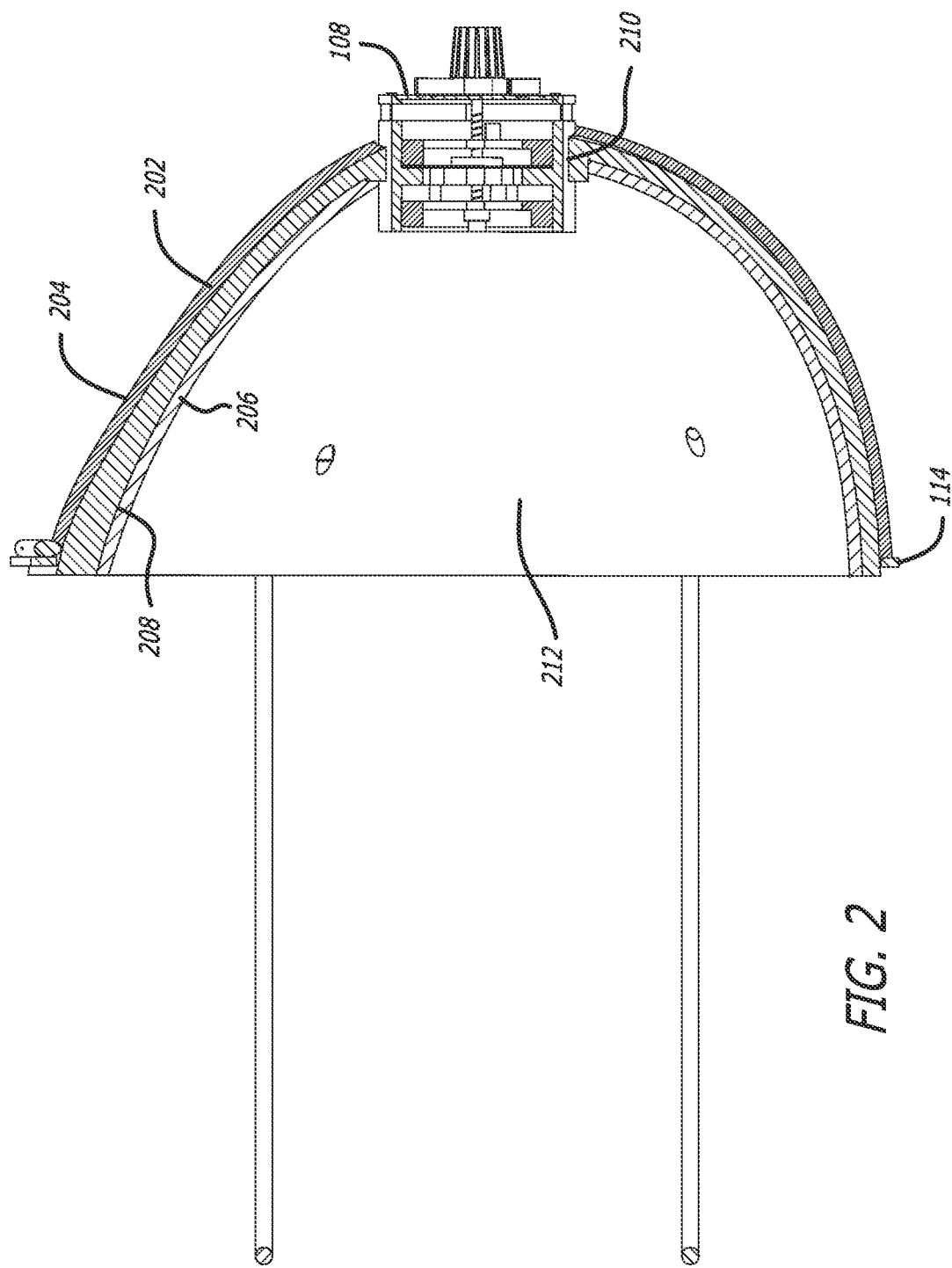
FIG. 2 is a cross-sectional view of the tri-mode filtering facepiece respirator of FIG. 1.

FIG. 2 is a cross-section view of filtering facepiece respirator 100. As shown, the facemask 102 may include a substantially dome-shaped mask body 202 comprising an outer porous layer 204, an inner porous layer 206, a filtering layer 208, and a valve port 210 formed in a front central portion of the mask body 202. The inner layer 206 defines an interior cavity 212 for enclosing the nose and mouth of the wearer.

The outer porous layer 204 may be molded using polyester fibers. The layer serves as an outer support layer and pre-filter. The inner porous layer 206 may also be formed as a fiberfill shell and may also be molded using polyester fibers. While the outer porous layer 204 and the inner porous layer 206 are described herein as being made from polyester fibers, in other implementations, the outer porous layer 204 and the inner porous layer 206 may be made from any other permeable fabric or material.

The inner and outer layers 204 and 206 may be made of different or the same material. For example, the outer layer 204 may be formed of larger fibers than the inner layer 206 so that the inner layer 206, by being formed of finer fibers, may have a softer and therefore more comfortable surface to lie against the face of the wearer.

As shown, the inner and outer layers 204 and 206 are configured to sandwich the filtering layer 208. The filtering layer 208 may be formed from any known type of filter material so as to provide for the filtering of particular elements in the air. For example, the filtering layer 208 may be composed of nonwoven, interlaced polypropylene fibers, but can also be made of electrospun nanofibers, activated charcoal-treated sheets or sheets formed from charcoal particles, fiberglass material, cellulose, or other natural materials. The filtering layer 208 should preferably be electrostatic, hydrophobic, and water and droplet-proof.

In preferred embodiments, the filtering layer 208 should be adapted to trap particles having a size range of known contaminants or pathogens. The filter layer 208 material may be chosen in response to the specific contaminants or pathogens sought to be sieved.

In other embodiments, the filtering layer 208 may comprise two or more layers of material having different filtering specifications, such that one layer filters larger particles and the other layers filter the specific smaller particles of interest. This arrangement may affect various performance parameters of the facemask 102.

In this way, inner and outer layers 204 and 206 are intended to be more porous than the filtering layer 208 and are constructed to continually sanitize contaminant particles trapped by filtering layer 208. In addition, the inner and outer layers 204 and 206 may further serve to sanitize contaminants passing therethrough prior to reaching filtering layers 208.

The use of three layers 204, 206, and 208, as shown in FIG. 2, is illustrative only and may vary depending upon the specific application of the filtering facepiece 100 and its performance specifications. For example, it may be useful to construct a mask using only a single filtering layer 208 and only a single porous layer 204, such that the filtering layer 208 is located closer to the wearer than layer 204. Such an arrangement would provide a simple respirator mask that filters particulate contaminants and sanitizes them to protect the wearer of the facepiece. Likewise, a simplified mask may be constructed just using filtering layer 208 and porous layer 206, such that layer 206 is located closer to the wearer of such a facepiece. This arrangement would provide a surgical-type mask that traps and sanitizes contaminants exhaled by the mask wearer. It should also be kept in mind that layers 204 and 206 may be used in combination with one or more filtering layers 208 to provide a facepiece suitable for serving either as a respirator or a surgical mask. Finally, to aid in facial recognition, in some embodiments, portions of the three layers 204, 206, and 208 as shown in FIG. 2 can be replaced with clear or translucent plastic or silicone.

Turning back to FIG. 1, in some embodiments, the outer contour 110 may be lined with a deformable edge member 114 extending around the peripheral edge of the mask body 102. The edge member 114 may be made of silicone, thermoplastic polyurethane (TPU), polyvinyl, or other suitable material. More specifically, the edge member 114 may be formed from any compressible resilient polymer with either fast or slow recovery properties. The edge member 114 may be coupled to the outer contour 110 by glue, bonding, or other suitable means.

As better shown in FIG. 2, the three layers 204, 206, and 208 may be sealed together by any suitable means, such as ultrasonic welding, about the periphery of the mask body 202 and the edge member 114 may be disposed around the sealed periphery of the mask body 202. The edge member 114 provides a seal between the facemask 102 and the face of the wearer to prevent air from seeping into or out of the interior cavity 212 along the outer contour 110.

Returning to FIG. 1, the facemask 102 may be secured on the wearer's face by the upper and lower harnesses 104 and 106. The upper harness 104 may comprise an elastic member 120 made of a band or string of material coupled to an upper portion of the facemask 102 at each of its opposing ends 122. The elastic member 120 is configured to extend around the back of the head of the wearer. The elastic member 120 may be made of nylon, rubber, cloth, or any other elastic material. The elastic member 120 may be coupled to the facemask 102 by bonding, welding, or other mechanical means.

The lower harness 106 may comprise an elastic member 130 made of a band or string of material coupled to a lower portion of the facemask 102 at each of its opposing ends 132. The elastic member 130 is configured to extend around the back of the upper neck of the wearer. The elastic member 130 may be made of nylon, rubber, cloth, or any other elastic material. The elastic member 130 may be coupled to the facemask 102 by bonding, welding, or other mechanical means.

The upper and lower harnesses 104 and 106 may be made of elastic material to provide an adjustable fit. In some embodiments, the upper and lower harnesses 104 and 106 may be adjustable about the head of the wearer by adjustable buckle fasteners, fasteners straps, or any other suitable means. In other embodiments, one end of the harness may be coupled to an upper portion of the facemask 102, while an opposing end of the harness may be coupled to an upper portion of the facemask 102 such that each harness fits around the wearer's ears to secure the facemask on the wearer's face.

As shown in FIGS. 1 and 2, the respiratory valve 108 may be coupled to a front central portion of the facemask 102. In this way, while in use, the respiratory valve 108 is positioned in front of the mouth of the wearer. Alternatively, the respiratory valve 108 may be coupled to the side of the facemask to aid in facial recognition when portions of the three layers 204, 206, and 208 are replaced with clear or translucent plastic or silicone.

As better shown in FIG. 2, the respiratory valve 108 is configured to sit within the valve port 210 and the respiratory valve 108 may be fixed to the mask body 202 by bonding, weldment, glue, or any other suitable means. In other embodiments, the respiratory valve 108 may be detachably coupled to the mask body 202 at the valve port 210. The respiratory valve 108 can therefore be part of a disposable mask, fully reusable mask, or a reusable mask with disposable components.

As shown, valve 108 may have an annual-shaped construction. In other embodiments, valve 108 may have a polygonal-shaped construction. In any embodiment, the shape and dimensions of valve 108 preferable correspond to the shape and dimensions of the valve port 210.

Figure 3:
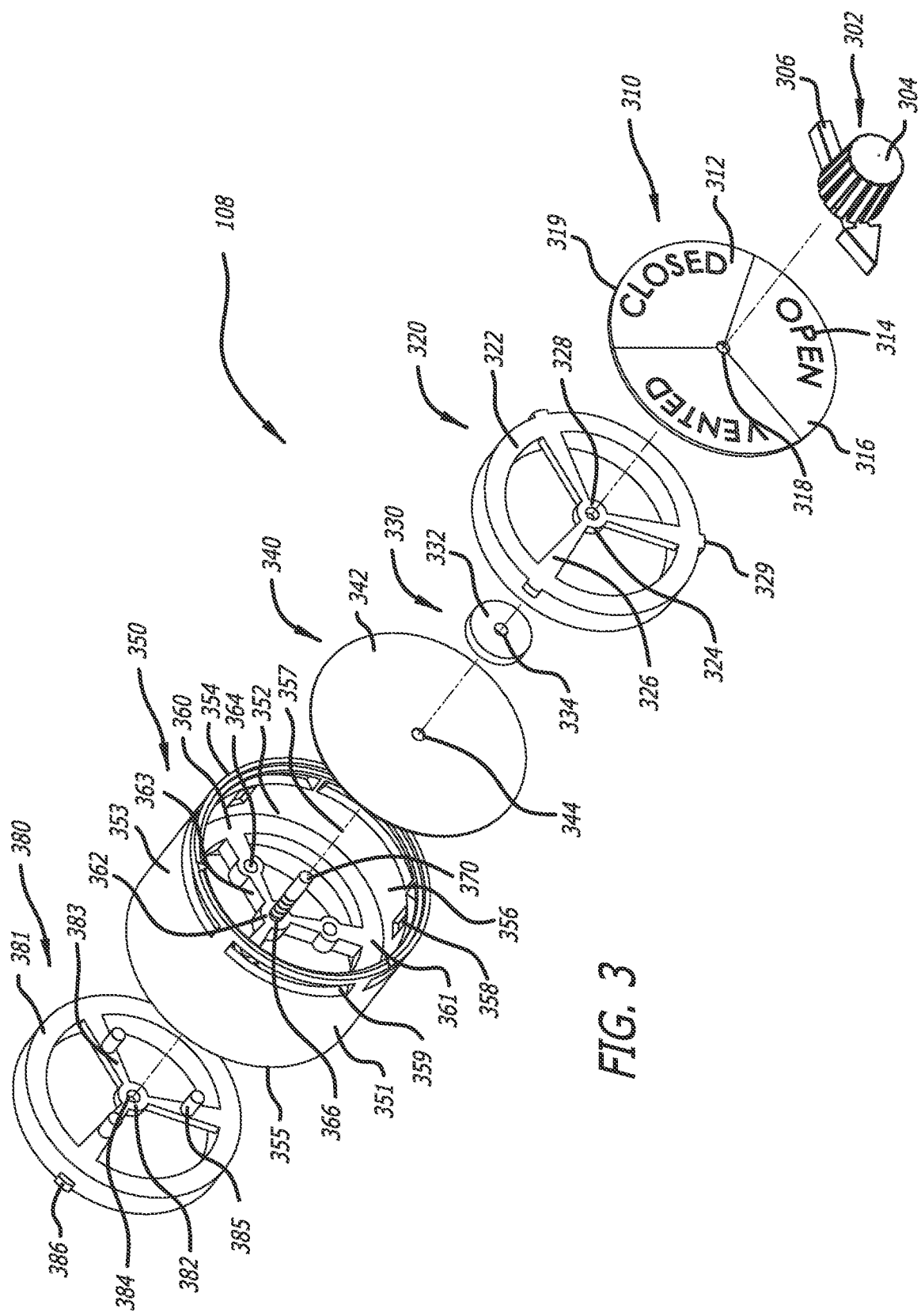
FIG. 3 is an exploded view of a respiratory valve of the tri-mode filtering facepiece respirator of FIG. 1.

FIG. 3 is an exploded view of the manual tri-mode respiratory valve 108. Moving from right to left, the respiratory valve 108 includes an adjustable dial 302, a valve cap indicator 310, an outer hub 320, a washer 330, a diaphragm 340, a valve housing 350, and an inner hub 380. Each respiratory valve 108 component may be made of plastic, lightweight metal, ceramic, or any other suitable material.

As shown, the adjustable dial 302 may include an arrow-shaped pointer 306 integrally formed with a dial knob 304. The dial knob 304 should be constructed to suitable dimensions enabling the wearer to turn the dial knob 304 with the wearer's fingers. In addition, the pointer 306 may be configured to complement indicia inscribed on valve cap indicator 310 to indicate to the wearer what operational mode the respiratory valve 108 is operating in. The adjustable dial 302 and its components may be constructed from plastic, aluminum, stainless steel, or any other suitable material.

The valve cap indicator 310 may comprise a thin-disc-shaped plate 312 having indicia 314 inscribed on its upper surface 316. In the embodiment shown, the indicia 314 includes the wording "OPEN," "VENTED," and "CLOSED" to correspond to the three modes of operation of the respiratory valve 108. In particular, the indicia 314, when the integrated pointer 306 of the adjustable dial 302 is positioned over the indicia, indicates to the wearer the mode of operation that the valve 108 is currently operating in.

The valve cap indicator 310 further includes a screw hole 318 for passing a screw member therethrough, as further described below, and an outer periphery 319. The outer periphery 319 is preferably constructed to diametrical dimensions that correspond to the diametrical dimensions of a first open end of the valve housing 350 such that the outer periphery 319 mates with an inner wall of the valve housing 350 to enclose the first end.

The valve cap indicator 310 may be constructed from plastic, aluminum, stainless steel, or any other suitable material. The indicia 314 may be inscribed or etched into the upper surface 316 of the valve cap indicator 310. In other embodiments, the indicia 314 may include stickers, light-emitting diodes, or may be painted on the upper surface 316 of the valve cap indicator 310. In some embodiments, the valve cap indicator 310 may include an auditory system, such as a transistor, to broadcast the mode of operation to the wearer.

Moving further downstream, the first movable hub member, outer hub 320 comprises an annular construction having an annual rim 322 coupled to a central hub portion 324 by a series of spokes 326 extending therebetween. The central hub portion 324 includes a threaded screw hole 328 for engaging a screw member extending therethrough, as described in further detail below. Each spoke 326 may be substantially triangular in shape, such that its thickness gradually increases as the spoke 326 extends from the central hub portion 324 towards the annual rim 322.

The outer hub 320 may further include a series of stabilizing tabs 329 formed about the periphery of the annual rim 322. The stabilizing tabs 329 are constructed to the dimensions and configured to fit within a corresponding series of elongated slots formed in the annular wall of the valve housing 350 to prevent the outer hub 320 from rotating as it is axially translated within the valve housing 350.

The outer hub 320 may be constructed to have a relatively thin thickness. For example, outer hub 320 may be constructed to a thickness of approximately 0.125 inches. The outer hub 320 may be constructed from plastic, aluminum, stainless steel, or any other suitable material.

The washer 330 may include a thin disc-shaped body 332 having an orifice 334 extending therethrough. The washer 330 secures the diaphragm 340 to the center of the valve housing 350 and serves as a bearing surface between the outer hub 320 and the diaphragm 340. The washer 330 may be constructed from plastic, aluminum, stainless steel, or any other suitable material.

Next, the diaphragm 340 may include a thin disc-shaped body 342 having an orifice 344 extending therethrough. The diaphragm 340, when secured in close proximity to a central hub housed within the valve housing 350, forms a hermetic seal to prevent airflow through the respiratory valve 108, as described in further detail below. The diaphragm 340 may be constructed from rubber, latex, polymers or any other suitable pliable material.

In other embodiments, the diaphragm 340 may be constructed from filtering media. In particular, the diaphragm 340 may be made of porous material that filters microscopic particulates. In such embodiments, air may be being filtered through the facemask 102 and the respiratory valve 108.

Moving further downstream, the valve housing 350 may comprise an annual body 351 having inner and outer annual walls 352 and 353 extending between a first open end 354 and an opposing open end 355. The inner annual wall 352 defines a chamber 356 for housing the diaphragm 340 and a longitudinal axis 357. The annual body 351 further includes a series of elongated slots 358 circumferentially disposed about the inner annual wall 352 and a series of arcuate-shaped vents 359 formed near the open end 354.

The elongated slots 358 are configured to receive corresponding stabilizing tabs 329 of the outer hub 320. The slots 358 are further constructed to dimensions corresponding to the width of the stabilizing tabs to restrict the outer hub 320 from rotating as it is axially translated within the valve housing 350. The vents 359 are configured to allow air to pass into and/or out of the chamber 356.

As mentioned above, the outer hub 320 may further include a series of stabilizing tabs 329 formed about the periphery of the annual rim 322 for fitting within a corresponding series of elongated slots formed in the annular wall of the valve housing 350. The stabilizing tabs 329 cooperate with the elongated slots to guide and assist the axial back-and-forth movement of outer hub 320 along the length of the valve housing 350 and prevent the outer hub 320 from rotating as it is translated within the housing 350.

A fixed hub 360 having an annular construction is coupled to the inner annual wall 352 in a central portion of the chamber 356. In the embodiment shown, the fixed hub 360 is integrally formed with the inner annual wall 352, but in other embodiments, the fixed hub 360 may be coupled to the inner annular wall 352 by bonding, welding, or any other suitable means.

The fixed hub 360 includes an annual rim 361 coupled to a central hub portion 362 by a series of spokes 363 extending therebetween. Each spoke 363 may be substantially triangular in shape, such that its thickness gradually increases as the spokes 363 extends from central hub portion 362 towards the annual rim 361. Each spoke 363 may include a spacer guide hole 364 formed approximately midway along its length for receiving a diaphragm spacer of the inner hub 385, as described in further detail below.

The central hub portion 362 includes a bore 366 extending therethrough. The bore 366 is positioned along the longitudinal axis 357. The bore 366 is constructed to receive an integrated screw member 370 extending therethrough along the longitudinal axis 357. As better shown in FIG. 4, the integrated screw member 370 is an elongated cylindrical body 402 having a center portion 404, a first end 406, a first threaded portion 408 extending between the center portion 404 and the first end 406, an opposing end 410, and a second threaded portion 412 extending between the center portion 404 and opposing end 410. In preferred embodiments, the diametrical dimensions of screw member 370 may complement the dimensions of bore 366 such that the center portion 404 of the integrated screw member 370 freely rotates inside of bore 366 as screw member 370 is rotated clockwise or counterclockwise.

As discussed in further detail below, the first threaded portion 408 is threadedly coupled to the outer hub 320 to translate the hub axially along the longitudinal axis 357 as the integrated screw member 370 is rotated clockwise or counterclockwise. Similarly, the second threaded portion 412 is threadedly coupled to inner hub 380 to translate the hub axially along the longitudinal axis 357 as the integrated screw member 370 is rotated clockwise or counterclockwise.

Returning to FIG. 3, the inner hub 380 comprises an annular construction having an annual rim 381 coupled to a central hub portion 382 by a series of spokes 383 extending therebetween. The central hub portion 382 includes a threaded screw hole 384 for engaging screw member 370 extending therethrough, as described in further detail below. Each spoke 383 may be substantially triangular in shape, such that its thickness gradually increases as the spoke 383 extends from the central hub portion 382 towards the annual rim 381.

The inner hub 380 may further include a series of cylindrical-shaped diaphragm spacers 385 outwardly extending from a corresponding spoke 383, and a series of stabilizing tabs 386 formed about the periphery of the annual rim 381. The diaphragm spacers 385 are constructed to diametrical dimensions that correspond to the diametrical dimensions of the spacer guide holes 364 formed in the spokes 363 of the fixed hub 360. The diaphragm spacers 385 are constructed to a height that is greater than the thickness of the fixed hub 360. The diaphragm spacers 385 are, further, configured to mate with and extend through the spacer guide holes 364 as the inner hub 380 is axially translated within the valve housing 350 towards the fixed hub 360. The spacer 385 aids to align the relative positions of the spokes of the inner hub 380, fixed hub 360, and outer hub 320 with one another to limit turbulence and promote laminar airflow through the valve chamber 356.

The stabilizing tabs 386 are constructed to the dimensions and configured to fit within a corresponding series of elongated slots (not shown) formed in the annular wall of the valve housing 350 to prevent the inner hub 380 from rotating as it is axially translated within the valve housing 350.

The inner hub 380 may be constructed to have a relatively thin thickness. For example, inner hub 380 may be constructed to a thickness of approximately 0.125 inches. The inner hub 380 may be constructed from plastic, aluminum, stainless steel, or any other suitable material.

As better shown in FIG. 4, the integrated screw member 370 is configured to extend the entire length of the respiratory valve 108 (i.e., from the valve cap indicator 310 to the inner hub 380) along the longitudinal axis 357. As shown, at one end, the first end 406 of the screw member 370 may be attached to the adjustable dial 302 at a seat 420 formed in the bottom of the knob 304. The adjustable dial 302 may be attached to the first end 406 by a sealant, glue, bond, snap-fit, interference fit, or other suitable means. The adjustable dial 302 is configured to rotate the integrated screw member 370 as the knob 304 is manually rotated by the wearer.

On the opposite end of the integrated screw member 370, opposing end 410 is threadedly coupled to the inner hub 380 at threaded screw hole 384.

In addition to being attached to the adjustable dial 302 and coupled to the inner hub 380, the integrated screw member 370 is, further, threadedly coupled to the outer hub 320. In this way, the first threaded portion 408 of the screw member 370 comprises male threads that correspond to female threads comprising the threaded screw hole 328 of the outer hub 320. Similarly, the second threaded portion 412 of the screw member 370 comprises male threads that correspond to female threads comprising the threaded screw hole 384 of the inner hub 380.

As such, when the screw member 370 is rotated by the adjustable dial 302, the male threads of the first threaded portion 408 engage the female threads of threaded screw hole 328 to translate the outer hub 320 axially along the longitudinal axis 357. Simultaneously, the male threads of the second threaded portion 412 engage the female threads of threaded screw hole 384 to translate the inner hub 380 axially along the longitudinal axis 357. Thus, as the screw member 370 is rotated by the adjustable dial 302, the outer hub 320 and the inner hub 380 are translated axially along the longitudinal axis 357 in tandem, spaced-apart relation.

In some embodiments, the respiratory valve 108 is operable in three modes of operation: an open mode, a vented mode, and closed mode.

FIGS. 4A and 4B illustrate the respiratory valve 108 in the open mode. In this mode, the adjustable dial 302 is turned counterclockwise and the inner hub 380 is translated along longitudinal axis 357 such that its annual rim 381 is positioned proximate to or abutting the annular rim 361 of the fixed hub 360. In this position, the diaphragm spacers 385 of the inner hub 380 extend through the spacer guide holes 364 to lift or urge the outer periphery of the diaphragm 340 away from the fixed hub 360 such that, when the wearer either inhales or exhales, air is permitted to freely and rapidly pass around the diaphragm 340, as shown by arrows 430. This permits the wearer to breathe through the valve 108 with minimal effort, thus, improving wearer comfort. This mode, however, provides minimum filtration through the filtering layer 208 of the facemask 102 and is for the breathing comfort of the wearer, only.

As best shown on FIG. 4C, the lengthwise dimensions of the elongated slots 358 define the distance that the inner hub 380 and the outer hub 320 are permitted to translate axially along the longitudinal axis 357.

FIGS. 5A and 5B illustrate the respiratory valve 108 in the vented mode. In this mode, the adjustable dial 302 is rotated clockwise from the open mode position. As the adjustable dial 302 is rotated clockwise, the inner hub 380 and the outer hub 320 are axially translated downstream in tandem, such that the inner hub 380 is translated axially along longitudinal axis 357 away from the fixed hub 360, while the outer hub 320 is translated axially along longitudinal axis 357 towards the fixed hub 360. In this position, the diaphragm spacers 385 of the inner hub 380 are disposed within the spacer guide holes 364 and the diaphragm 340 is no longer being lifted away from the fixed hub 360. The outer periphery of the diaphragm 340 may be lifted or urged away from the fixed hub 360 by air pressure when the wearer exhales, but drawn towards the fixed hub 360 by negative pressure to form a seal with the annual rim 361 when the wearer inhales. In this mode, exhaled air is permitted to pass around the diaphragm 340 and is exhausted through vents 359, as shown by arrows 530, thereby improving user comfort when the wearer exhales. But ambient air is prevented from passing through the valve 108 when the wearer inhales. This permits the wearer to exhale air through the valve 108 with minimal effort, but ambient air must be filtered through the filtering layer 208 of the facemask 102 when the wearer inhales.

FIGS. 6A and 6B illustrate the respiratory valve 108 in the closed mode. In this mode, the adjustable dial 302 is rotated clockwise from the vented mode position. As the adjustable dial 302 is further rotated clockwise, the inner hub 380 and the outer hub 320 are axially translated downstream in tandem, such that the inner hub 380 is translated axially along longitudinal axis 357 further away from the fixed hub 360, while the outer hub 320 is translated axially along longitudinal axis 357 towards the fixed hub 360 until annual rim 322 is positioned proximate to or abutting the annular rim 361 of the fixed hub 360. In this position, the diaphragm spacers 385 of the inner hub 380 are disposed within the spacer guide holes 364 and the outer periphery of the diaphragm 340 is sandwiched between annual rim 322 and annular rim 361 such that the diaphragm 340 is secured against the spokes 363 and annular rim 361 of the fixed hub 360. In this mode, air is prevented from passing in or out of the valve 108 when the wearer inhales and exhales. Thus, air will only pass through the filtering layer 208 of the facemask 102 when the wearer inhales and exhales, for optimum safety.

In sum, to close the valve 108, the adjustable dial 302 is turned clockwise and the outer hub 320 is advanced towards the center of the valve. When the adjustable dial 302 is completely turned and reaches a stop, the outer hub 320 will have secured the diaphragm 340 against the fixed hub 360, completely sealing the valve 108. When the adjustable dial 302 is turned in the opposite direction (i.e., counterclockwise), the outer hub 320 is moved away from the fixed hub 360, and the inner hub 380 is moved toward the fixed hub 360. When the adjustable dial 302 is completely turned in the opposite direction and reaches a stop, the diaphragm spacers 385 on the inner hub 380, lift or urge the diaphragm 340 away from center hub spokes 363 to open the valve 108 for air to flow freely therethrough. In instances when the diaphragm 340 is not secured to the fixed hub 360 by the outer hub 320 and not elevated by the spacers 385 of the inner hub 380, the valve 108 is vented and allows air to pass through the valve 108 during exhalation, but not during inhalation.

As illustrated in FIGS. 4 through 6, when the adjustable dial 302 is rotated clockwise from the open mode position to the closed mode position, the distance between the outer hub 320 and the fixed hub 360, depicted as arrow 460, gradually narrows until the outer hub 320 abuts the fixed hub 360. As the distance 460 narrows, the outer periphery of the diaphragm 340 becomes more restricted from being lifted or urged away from the spokes 363 of the fixed hub 360 by air pressure. Thus, as the adjustable dial 302 is rotated clockwise, breathing through the valve 108 becomes more restricted for the wearer until air is no longer permitted to pass in and out of the valve 108 in the closed mode. Therefore, the wearer may adjust the adjustable dial 302 clockwise or counterclockwise until the suitable level of breathing comfort is obtained.

Figure 7:
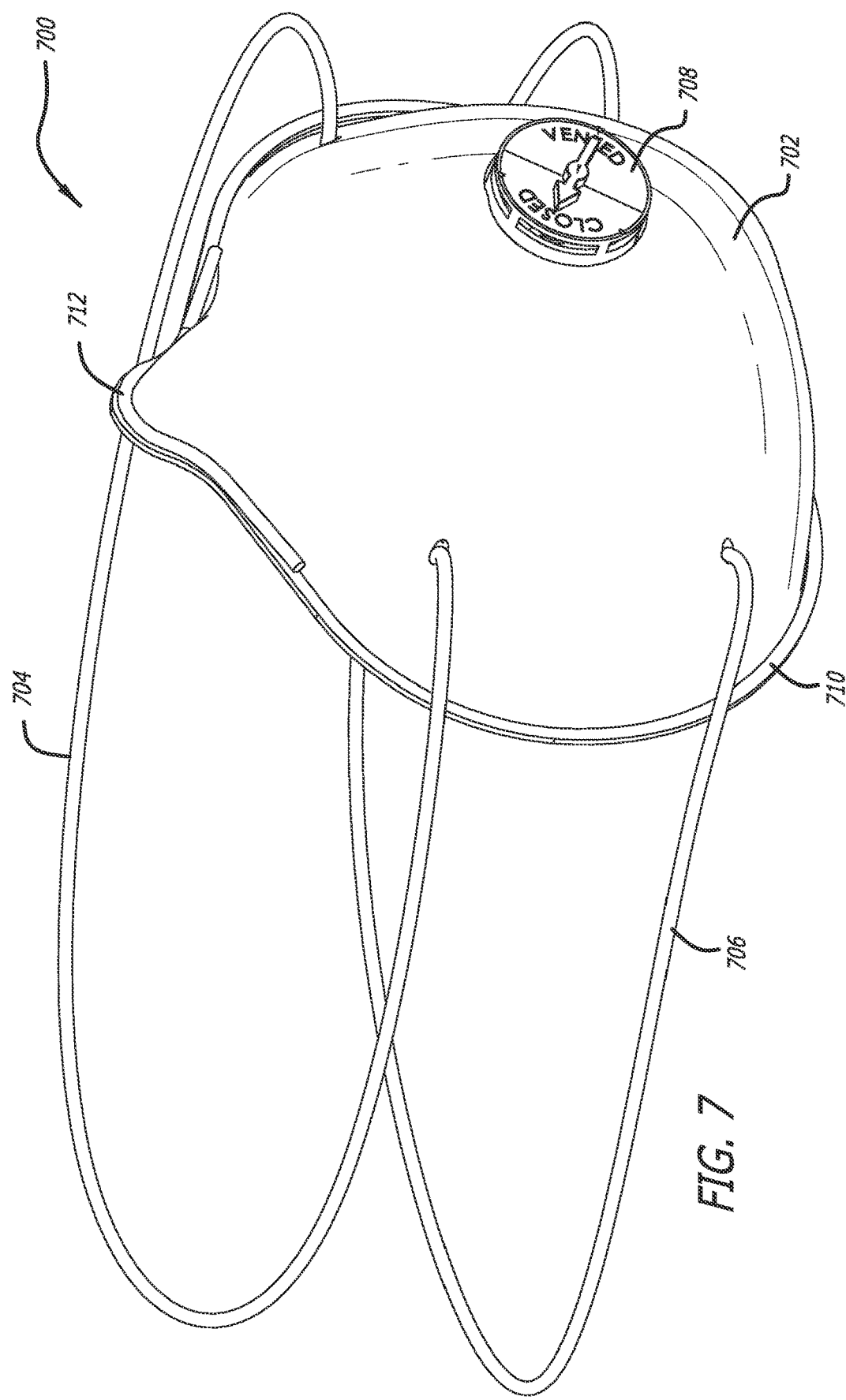
FIG. 7 is a perspective view of an example of a motorized bi-mode filtering facepiece respirator in accordance with the teachings of the present disclosure.

FIG. 7 is a perspective view of another example of a filtering facepiece respirator 700 according to the teaching of the present disclosure. As shown, the facepiece respirator 700 may include a facemask 702, an upper harness 704 coupled to an upper portion of the face mask 702, a lower harness 706 coupled to a lower portion of the facemask 702, and a respiratory valve 708 coupled to a central front portion of the face mask 702. In preferred implementations, the face mask 702 may include an outer contour 710 defined about the peripheral edge of the facemask 702 to substantially cover the nose and mouth of a wearer and a bendable reinforcement nosepiece 712 coupled to an upper portion of the outer contour 710. For purposes of simplicity, the facemask 702, upper harness 704, and lower harness 706 may be constructed similar to the facemask 102, upper harness 104, and lower harness 106 of facepiece respirator 100, thus, the details of these components will not be described further.

Figure 8:
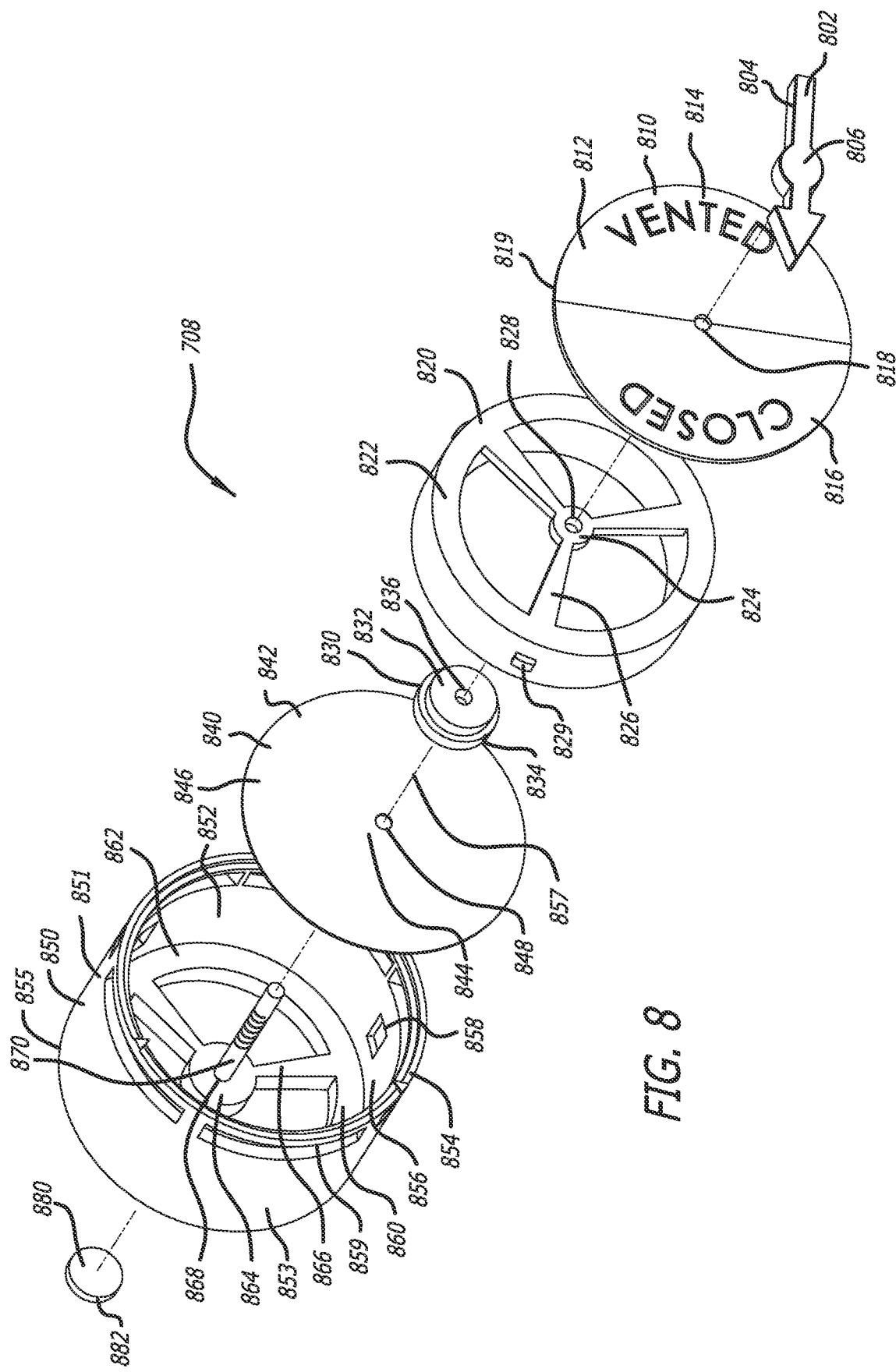
FIG. 8 is an exploded view of a respiratory valve of the bi-mode filtering facepiece respirator of FIG. 7.

FIG. 8 is an exploded view of respiratory valve 708. In this example, the respiratory valve 708 is a motorized adjustable bi-mode valve. Moving from right to left, the respiratory valve 708 includes a rotatable pointer 802, a valve cap indicator 810, an outer hub 820, a multifunctional motor module 830, a diaphragm 840, a valve housing 850, and a multifunctional battery module 880.

As shown, the pointer 802 may comprise an arrow-shaped pointer body 804 and a pointer hub 806. The pointer 802 be constructed to suitable dimensions complementing indicia inscribed on valve cap indicator 810 to indicate to the wearer what operational mode the respiratory valve 708 is operating in. The pointer 802 may be constructed from plastic, aluminum, stainless steel, or any other suitable material.

The valve cap indicator 810 may comprise thin-disc-shaped plate 812 having indicia 814 inscribed on its upper surface 816. In the embodiment shown, the indicia 812 includes the wording "VENTED" and "CLOSED" to correspond to the two modes of operation of the respiratory valve 708. In particular, the indicia 812, when the pointer 802 is positioned over the indicia, indicates to the wearer the mode of operation that the valve 708 is currently operating in.

The valve cap indicator 810 further includes a screw hole 818 for passing a screw member therethrough, as further described below, and an outer periphery 819. The outer periphery 819 is preferably constructed to diametrical dimensions that correspond to the diametrical dimensions of a first open end of the valve housing 850 such that the outer periphery 819 mates with an inner wall of the valve housing 850 to enclose the first end.

The valve cap indicator 810 may be constructed from plastic, aluminum, stainless steel, or any other suitable material. The indicia 814 may be inscribed or etched into the upper surface 816 of the valve cap indicator 810 or, in other embodiments, the indicia 814 may include stickers, light-emitting diodes, or may be painted on the of the upper surface 816 of the valve cap indicator 810.

Moving further downstream, the outer hub 820 comprises an annular construction having an annual rim 822 coupled to a central hub portion 824 by a series of spokes 826 extending therebetween. The central hub portion 824 includes a threaded screw hole 828 for engaging a screw member extending therethrough. Each spoke 826 may be substantially triangular in shape, such that its thickness gradually increases as the spoke 826 extends from the central hub portion 824 towards the annual rim 822.

The outer hub 820 may further include a series of stabilizing tabs 829 formed about the periphery of the annual rim 822 for mating with a corresponding series of elongated slots 858 formed in the annular wall of the valve housing 850. The stabilizing tabs 829 cooperate with the elongated slots 858 to guide the axial back-and-forth movement of the outer hub 820 along the length of the valve housing 850 and prevent the outer hub 820 from rotating as it is translated inside of the housing 850.

The outer hub 820 may be constructed to have a relatively thin thickness. For example, outer hub 820 may be constructed to a thickness of approximately 0.125 inches. The outer hub 820 may be constructed from plastic, aluminum, stainless steel, or any other suitable material.

The multifunctional motor module 830 may include a thin disc-shaped motor 832, a thin disc-shaped motor base 834, and an orifice 836 extending therethrough. The motor module 830 serves to secure an inner peripheral region of the diaphragm 840 to a central support structure in the valve housing 850 and to rotate an integrated screw member extending through the center of the valve 708, as described in further detail below. The motor 832 may comprise, for example, a low-profile rotary solenoid actuator, and the motor base 834 may be constructed from plastic, aluminum, stainless steel, or any other suitable material.

Next, the diaphragm 840 may include a thin disc-shaped body 842 having an inner peripheral region 844, an outer peripheral region 846, and an orifice 848 extending therethrough. Similar to diaphragm 340, diaphragm 840, when secured in close proximity to a central hub housed within the valve housing 850, forms a hermetic seal to prevent airflow through the respiratory valve 708, as described in further detail below. The diaphragm 840 is preferably constructed from rubber, latex, polymers, or any other non-porous pliable material. In other embodiments, the diaphragm 840 may be constructed from filtering media.

Moving further downstream, the valve housing 850 may comprise an annual body 851 having inner and outer annual walls 852 and 853 extending between a first open end 854 and an opposing open end 855. The inner annual wall 852 defines a chamber 856 for housing the diaphragm 840, motor module 830, and outer hub 820, and a longitudinal axis 857. The annual body 851 further includes a series of elongated slots 858 circumferentially disposed about the inner annual wall 852 and a series of arcuate-shaped vents 859 formed near the open end 854.

The elongated slots 858 are configured to receive corresponding stabilizing tabs 829 of the outer hub 820. The slots 858 are further constructed to dimensions corresponding to the width of the stabilizing tabs 829 to restrict the outer hub 820 from rotating as it is axially translated within the valve housing 850. The vents 859 are configured to allow air to pass into and/or out of the chamber 856.

A fixed hub 860 having an annular construction is coupled to the inner annual wall 852 in an aft portion of the chamber 856. In the embodiment shown, the fixed hub 860 integrally formed with the inner annual wall 852, but in other embodiments, the fixed hub 860 may be coupled to the inner annular wall 852 by bonding, welding, or any other suitable means.

The fixed hub 860 includes an annual rim 862 coupled to a central hub portion 864 by a series of spokes 866 extending therebetween. Each spoke 866 may be substantially triangular in shape, such that its thickness gradually increases as the spokes 866 extends from central hub portion 864 towards the annual rim 862.

The central hub portion 864 includes a tap hole 868 extending substantially. The tap hole 868 is positioned along the longitudinal axis 857. The tap hole 868 is constructed to receive an integrated screw member 870 extending therethrough along the longitudinal axis 857. As better shown in FIG. 9B, the integrated screw member 870 is an elongated cylindrical body 902 having a first end 904, an opposing end 906, a threaded portion 908 extending between the first end 904 and the opposing end 906.

Returning to FIG. 8, the multifunctional battery module 880 may comprise a body 882 comprising a thin-disc construction. In other embodiments, the body 882 of the multifunctional battery module 880 may be constructed to other geometrical shapes. As better shown in FIG. 9B, the multifunctional battery 880 may be coupled to a surface of the central hub portion 864 by bonding, welding or other mechanical means. The multifunctional battery module 880 may be electrically coupled by wiring to the multifunctional motor module 830 to power the motor 832 and electronic circuitry (not shown) controlling the motor 832. In other embodiments, the multifunctional battery module 880 and the multifunctional motor module 830 may include other features, such as, but not limited to, wireless communications between the facepiece and a mobile device or computer and the monitoring of air quality within the facemask.

The automated respiratory valve 708 may be operable in two modes of operation: a vented mode and closed mode. FIGS. 9A and 9B illustrate the respiratory valve 708 in the vented mode.

As shown, the integrated screw member 870 is configured to extend the entire length of the respiratory valve 708 (i.e., from the valve cap indicator 810 to the fixed hub 860) along the longitudinal axis 857. At one end, the opposing end 906 of the screw member 870 may be attached to the rotatable pointer 802 at a seat 920 formed in the bottom of the pointer hub 806. The pointer 802 may be attached to opposing end 906 by a sealant, glue, bond, snap-fit, interference fit, or other suitable means. The motor 832 is configured to rotate the integrated screw member 870 and the attached pointer 802 between a vented mode position and a closed mode position via electronic circuitry (not shown).

On the opposite end, first end 904 may be received by the tap hole 868 in the central hub portion 864 of the fixed hub 860. In some embodiments, the tap hole 868 may be dimensioned such that the first end 904 of the integrated screw member 870 is permitted to rotate freely within hole 868. In other embodiments, the first end 904 of the integrated screw member 870 may be rotatably coupled to roller bearings installed in the tap hole 868.

As further shown, the inner peripheral region 844 of the diaphragm 840 may be fixedly attached to a surface of the central hub portion 864 by, for example, glue, sealant, or bonding. Similarly, the base 834 of the motor module may be fixed atop the inner peripheral region 844 of the diaphragm 840 by, for example, glue, sealant, or bonding. According to this construction, the inner peripheral region 844 of the diaphragm 840 is fixed in place, while the outer peripheral region 846 of the diaphragm 840 may be permitted to be urged or otherwise moved away from spokes 866 and annular rim 862 of the fixed hub 860, thus permitting air to flow around the diaphragm 840 and through the valve chamber 856.

Upstream, the male threads of the threaded portion 908 of the screw member 870 are configured to engage the female threads of the threaded screw hole 828 of the outer hub 820 to translate the hub axially along the longitudinal axis 857 as the screw member 870 is rotated clockwise or counterclockwise. The stabilizing tabs 829 (FIG. 8) are configured to mate or fit within the elongated slots 858 to guide the outer hub 820 as it translates within the chamber 856 and, further, prevents the outer hub 820 from rotating about the screw member 870 as the outer hub 820 is axially translated.

In the vented mode, the outer hub 820 is positioned along longitudinal axis 857 such that its annual rim 822 of the outer hub 820 is spaced apart from the annular rim 862 of the fixed hub 860. In this position, the spacing between annual rim 822 and annular rim 862 permits the outer peripheral region 846 of the diaphragm 840 to be lifted or urged away from the annular rim 862 and spokes 866 of the fixed hub 860 by air pressure when the wearer exhales, however, the outer peripheral region 846 of the diaphragm 840 is drawn towards the fixed hub 860 by negative pressure to form a seal with annual rim 862 when the wearer inhales. In this mode, exhaled air is permitted to pass around the diaphragm 840 and is exhausted through vents 859, as shown by arrows 930, thereby improving user comfort when the wearer exhales. But ambient air is prevented from passing through the valve 708 when the wearer inhales. This permits the wearer to exhale air through the valve 708 with minimal effort, but ambient air must be filtered through the filtering layer of the facemask 702 when the wearer inhales.

FIGS. 10A and 10B illustrate respiratory valve 708 in the closed mode. In this mode, the integrated screw member 870 and the attached pointer 802 are rotated clockwise from the vented mode position by a controller (not shown) electrically connected to the motor module 830. In particular, as the controller is commanded by the wearer to operate in the closed mode, the controller transmits an electric signal to the motor module 830 to start the motor 832 and the motor 832 rotates the screw member 870 clockwise from a vented position to a closed position. Commands may be transmitted by the wearer to the controller by, for example, wireless connection, such as a mobile application stored on and activated from a mobile device. When the wearer decides that it wants to return the mask back to is vented mode of operation, the wearer may activate the controller to reserve the motor 832, thus rotating the screw member 870 counterclockwise from the closed position to the vented position.

Other embodiments may include additional functions of the multifunctional motorized motor module 830 include but are not limited to communication to and from the mask and sensing of conditions within the mask.

As the screw member 870 is rotated clockwise, the male threads of the threaded portion 908 of the screw member 870 engage the female threads of the threaded screw hole 828 of the central hub portion 824 of the outer hub 820 to axially translate the outer hub 820 towards the fixed hub 860. When the outer hub 820 is translated to the closed mode position, the annual rim 822 of the outer hub 820 is positioned proximate to or abutting the annular rim 862 of the fixed hub 860. In this position, the outer peripheral region 846 of the diaphragm 840 is sandwiched between the annular rim of the outer hub 822 and the annular rim of the fixed hub 862 such that the diaphragm 840 is secured against the annual rim of the outer hub 822 and annular rim of the fixed hub 862 and the spokes 866 of the fixed hub 860. In this mode, the valve 708 is completely sealed and air is prevented from passing in or out of the valve 708 when the wearer inhales and exhales. Thus, air will only pass through the filtering layers of the facemask 702 when the wearer inhales and exhales, for optimum safety.

Figure 11:
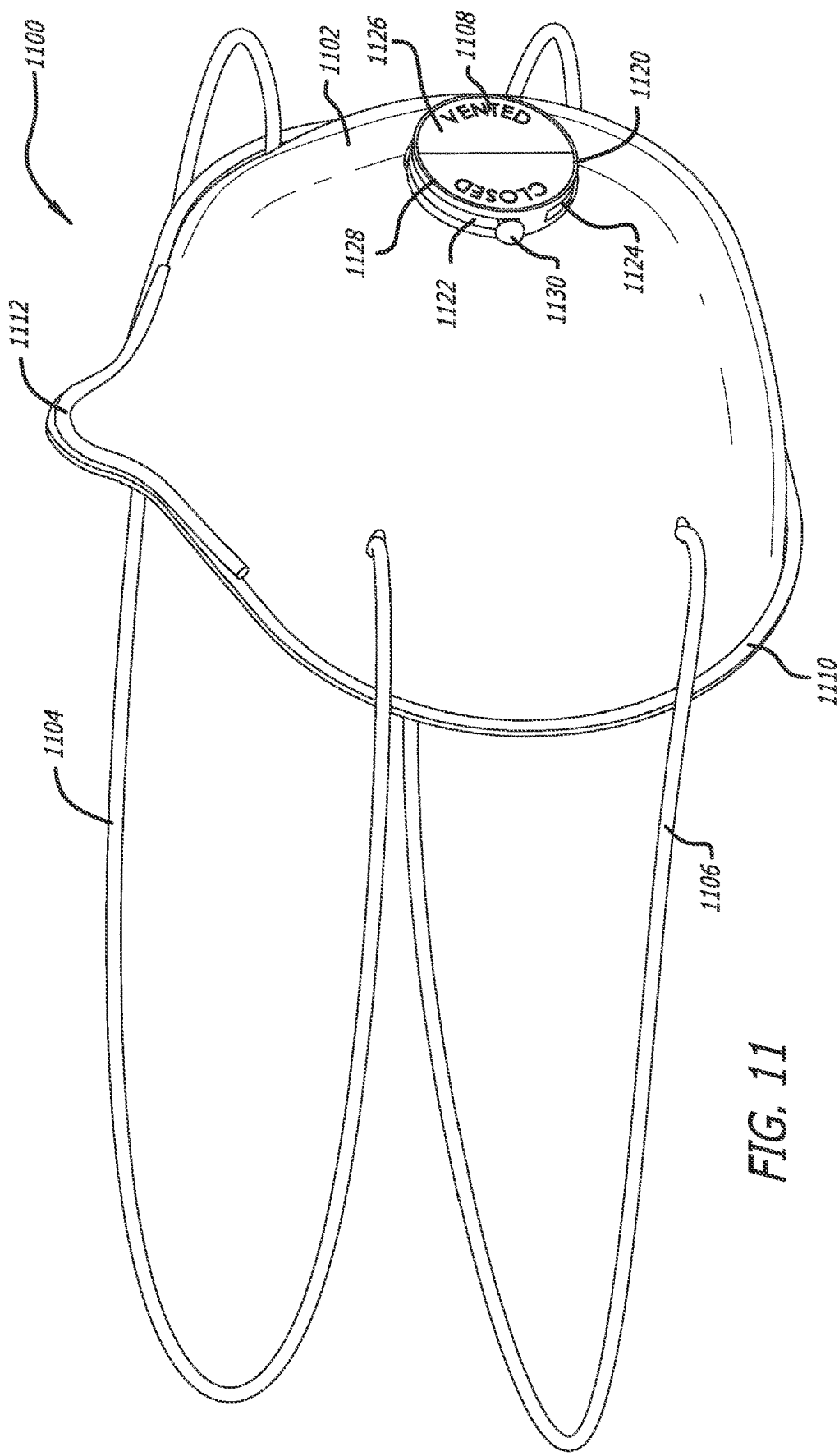
FIG. 11 is a perspective view of an example of a manual bi-mode facepiece respirator with a rotating valve controller, in accordance with the teachings of the present disclosure.

FIG. 11 is a perspective view of a third example of a filtering facepiece respirator 1100 according to the teaching of the present disclosure. As shown, the facepiece respirator 1100 may include a facemask 1102, an upper harness 1104 coupled to an upper portion of the face mask 1102, a lower harness 1106 coupled to a lower portion of the facemask 1102, and a respiratory valve 1108 coupled to a central front portion of the face mask 1102. In preferred implementations, the face mask 1102 may include an outer contour 1110 defined about the peripheral edge of the facemask 1102 to substantially cover the nose and mouth of a wearer and a bendable reinforcement nosepiece 1112 coupled to an upper portion of the outer contour 1110. For purposes of simplicity, the facemask 1102, upper harness 1104, and lower harness 1106 may be constructed similar to the facemask 102, upper harness 104, and lower harness 106 of facepiece respirator 100, thus, the details of these components will not be described further.

As shown in this example, the respiratory valve 1108 is a bi-mode valve with a rotatable valve gate that's operable in a vented mode of operation and a closed mode of operation. As shown, respiratory valve 1108 may include a valve housing 1120, a rotatable valve gate 1130 having an arm portion that's slidable within a slot 1122 formed along the periphery of the valve housing 1120, and a valve cap indicator 1126.

In the example shown, the valve housing 1120 comprises a thin, disc-shaped construction, but in other embodiments, the construction of the valve housing 1120 may include other suitable geometric shapes. The valve housing 1120 further includes one or more vents 1124 for expelling air out of valve 1120. The valve housing 1120 and its components may be constructed from plastic, aluminum, stainless steel, or any other suitable material.

The valve cap indicator 1126 may comprise a thin-disc-shaped plate having indicia inscribed on its upper surface. In the embodiment shown, the indicia includes the wording "VENTED" and "CLOSED" to correspond to the two modes of operation of the respiratory valve 1108. The valve cap indicator 1126 may include an outer periphery 1128 preferably constructed to diametrical dimensions that correspond to the diametrical dimensions of valve housing 1120 such that the outer periphery 1128 mates with an open end of the valve housing 1120 to enclose housing.

The valve cap indicator 1126 may be constructed from plastic, aluminum, stainless steel, or any other suitable material. The indicia may be inscribed or etched into the upper surface of the valve cap indicator 1126. In other embodiments, the indicia may include stickers, light-emitting diodes, or may be painted on the upper surface of the valve cap indicator 1126.

Figures 12A, 12B:
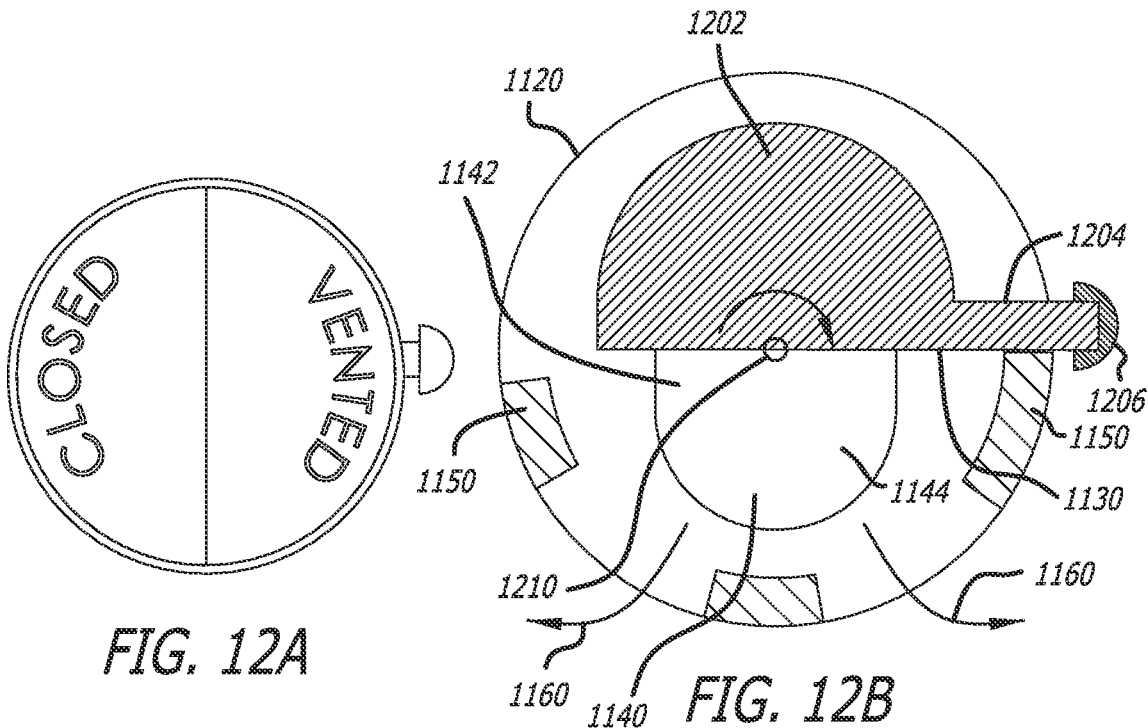
FIG. 12A is a front view of a respiratory valve of the bi-mode filtering facepiece respirator of FIG. 11 in a "vented" mode of operation.
FIG. 12B is a cross-sectional view of the respiratory valve of FIG. 12A in a "vented" mode of operation.

As mentioned above, the manual bi-mode respiratory valve 1108 may be operable in two modes of operation: a vented mode and closed mode. FIGS. 12A and 12B illustrate the respiratory valve 1108 in the vented mode.

As shown, the valve gate 1130 may include a gate body 1202, an integrated gate arm 1204, and an arm cap 1206. In the example shown, the gate body 1202 comprises a substantially semi-circular-shaped construction. The gate body 1202 is rotatably coupled to the valve housing 1120 by a pivot 1210. The pivot 1210 may include a dowel pin, bearing assembly, or other suitable means.

Respiratory valve 1108 further includes a diaphragm 1140. As shown, the diaphragm 1140 comprises a substantially elongated body 1142 having a fixed end 1302 (FIG. 13) and a free end 1144. The diaphragm 1140 is preferably constructed from rubber, latex, polymers, or any other non-porous pliable material.

In other embodiments, the diaphragm 1140 may be constructed from filtering media. In particular, the diaphragm 1140 may be made of porous material that filters microscopic particulates. In such embodiments, air is being filtered through the facemask 1102 and the respiratory valve 1108.

The fixed end 1302 may be secured to the valve housing 1120 by glue, bonding, or other suitable means. The free end 1144, shown in this example as being semi-circular in shape, is configured such that it may be urged or otherwise moved away from the valve housing 1120 under positive pressure to permit air to pass from the valve 1108 when the wearer exhales. But the free end 1144 is also configured such that it may be drawn toward the valve housing 1120 under negative pressure to create a seal between the free end 1144 and the valve housing 1120 that prevents air from passing into the valve 1108 when the wearer inhales.

Respiratory valve 1108 further includes a set of arcuate-shaped stops 1150. The stops are configured to restrict the rotational movement of the valve gate 1130 about the pivot 1210.

In the vented mode, as shown in FIG. 12B, the gate body 1202 is rotated clockwise about the pivot 1210 by the arm cap 1206 such that the gate body 1202 is positioned over the fixed end 1302 (FIG. 13B) of the diaphragm 1140 while the free end 1144 is uncovered and permitted to be urged away from the valve housing 1120 under positive pressure. This allows air to flow freely through the valve 1108 when the wearer exhales, as shown by arrows 1160, but air is prevented from flowing through the valve 1108 when the wearer inhales.

Figures 13A, 13B:
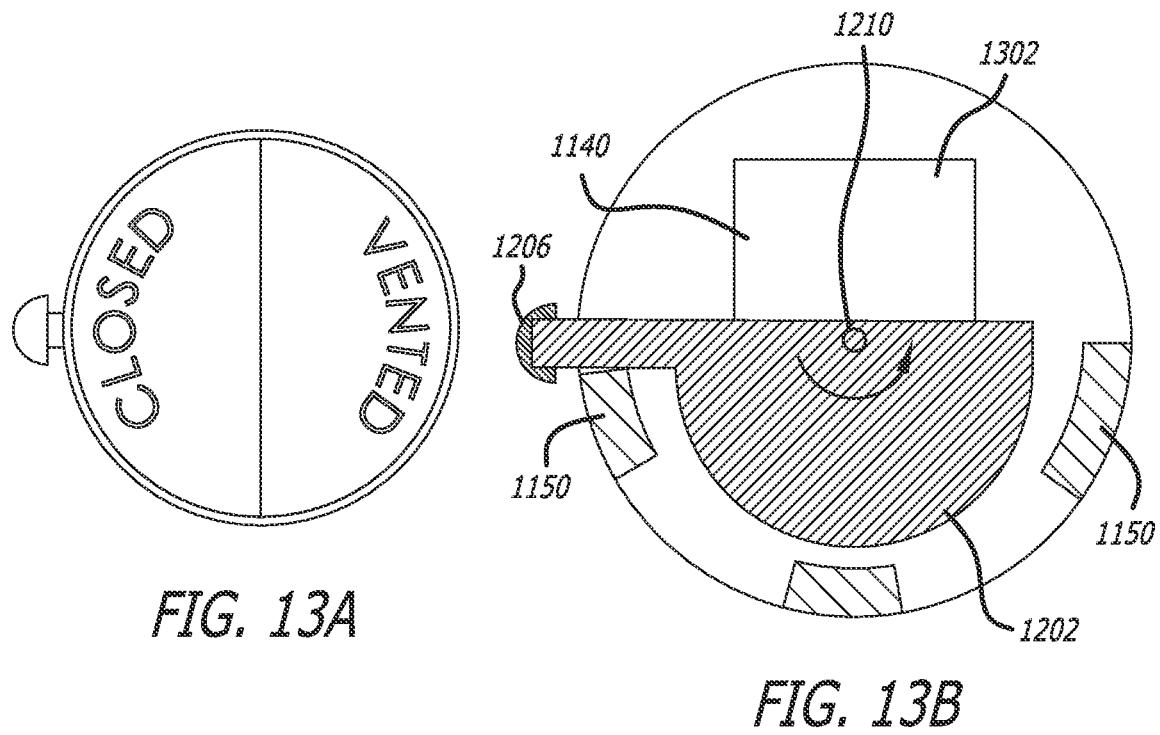
FIG. 13A is a front view of the respiratory valve of FIG. 12A in a "closed" mode of operation.
FIG. 13B is a cross-sectional view of the respiratory valve of FIG. 12A in a "closed" mode of operation.

FIGS. 13A and 13B illustrate the respiratory valve 1108 in the closed mode. In the closed mode, the gate body 1202 is rotated counterclockwise about the pivot 1210 by engaging the arm cap 1206 such that the gate body 1202 is positioned over the free end 1144 of the diaphragm 1140, thus abutting the free end 1144 against the valve housing 1120. This prevents air from flowing through valve 1108 when the wearer inhales or exhales. Therefore, air will only pass through the filtering layers of the facemask 1102 when the wearer inhales and exhales, for optimum safety.

Figure 14:
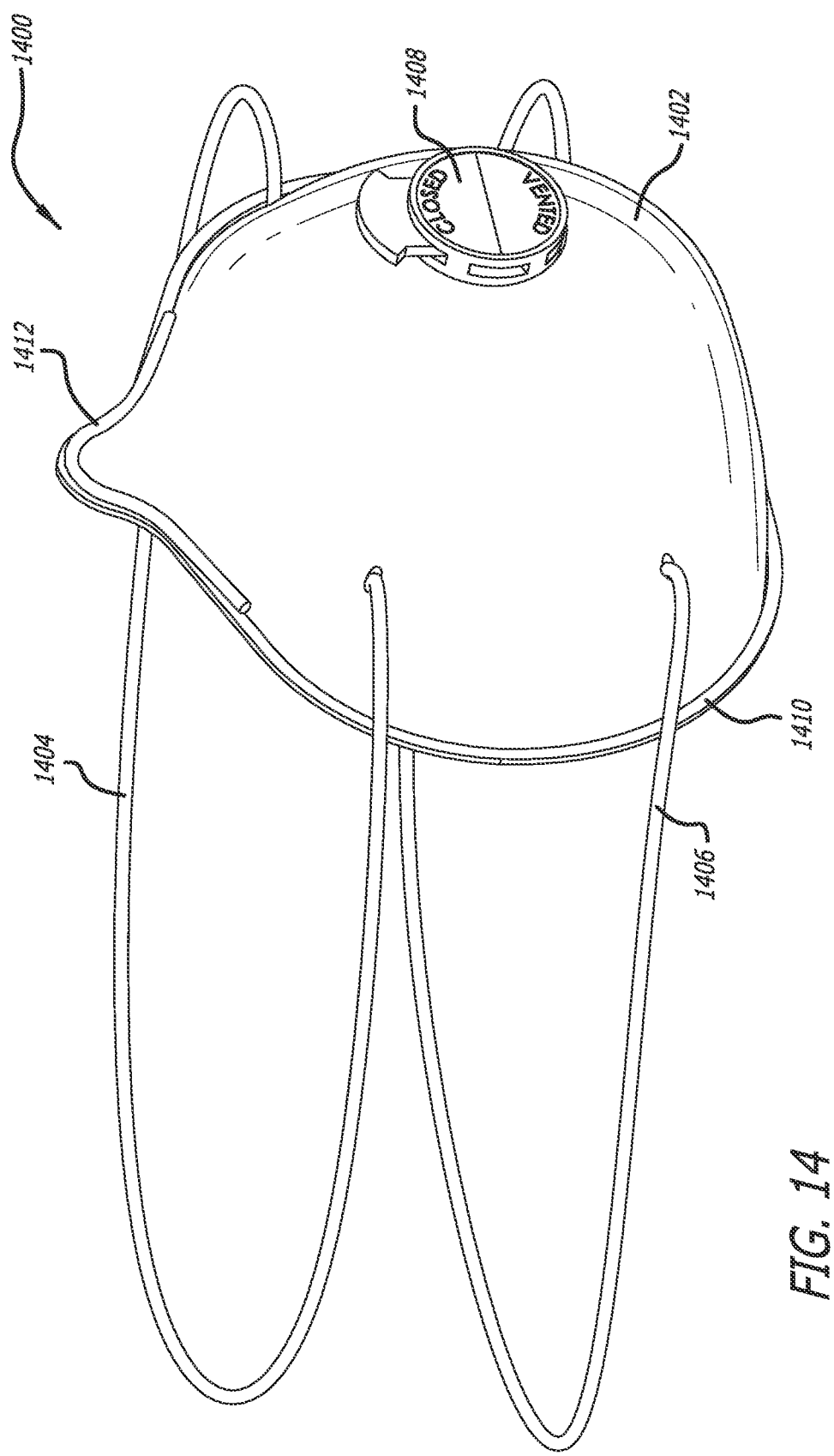
FIG. 14 is a perspective view of an example of a manual bi-mode sliding controller valve facepiece respirator in accordance with the teachings of the present disclosure.

FIG. 14 is a perspective view of a fourth example of a filtering facepiece respirator 1400 according to the teaching of the present disclosure. As shown, the facepiece respirator 1400 may include a facemask 1402, an upper harness 1404 coupled to an upper portion of the face mask 1402, a lower harness 1406 coupled to a lower portion of the facemask 1402, and a respiratory valve 1408 coupled to a central front portion of the face mask 1402. In preferred implementations, the face mask 1402 may include an outer contour 1410 defined about the peripheral edge of the facemask 1402 to substantially cover the nose and mouth of a wearer and a bendable reinforcement nosepiece 1412 coupled to an upper portion of the outer contour 1410. For purposes of simplicity, the facemask 1402, upper harness 1404, and lower harness 1406 may be constructed similar to the facemask 102, upper harness 104, and lower harness 106 of facepiece respirator 100, thus, the details of these components will not be described further.

Figure 15:
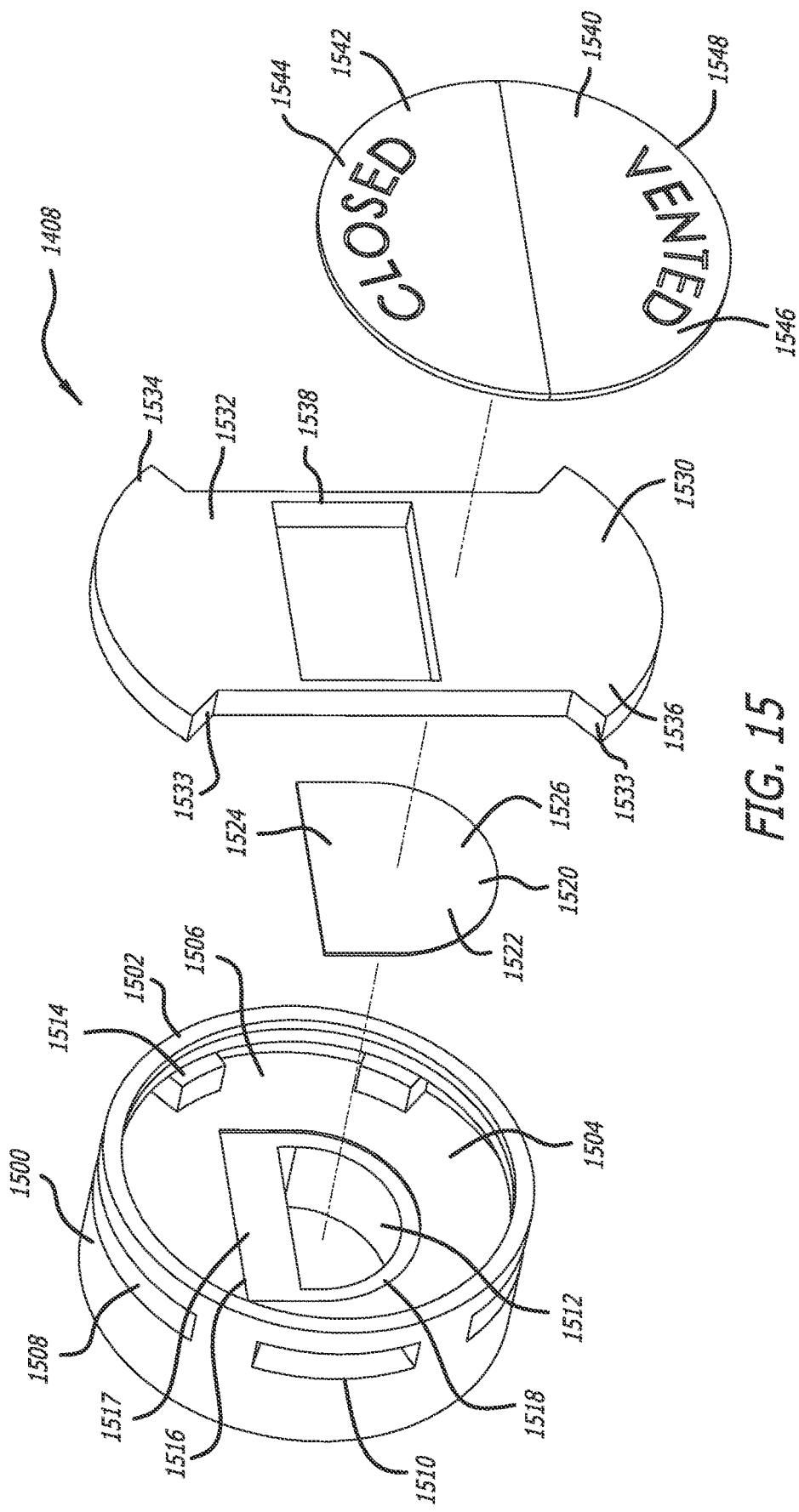
FIG. 15 is an exploded view of a respiratory valve of the bi-mode filtering facepiece respirator of FIG. 14.

FIG. 15 is an exploded view of respiratory valve 1408. In this example, the respiratory valve 1408 is a bi-mode valve with a slidable valve gate that's operable in a vented mode of operation and a closed mode of operation. As shown, respiratory valve 1408 may include a valve housing 1500, a diaphragm 1520, a slidable valve gate 1530, and a valve cap indicator 1540.

In the example shown, the valve housing 1500 comprises an annular wall 1502 and an internal landing region 1504. The annual wall 1502 and the landing region 1504 define a cell 1506 that houses the diaphragm 1520 and valve gate 1530. The valve housing 1500 further includes a pair of slots 1508 and vents 1510 formed in the annular wall 1502, a substantially semi-circular orifice 1512 extending through the center of the landing region 1504, and series of arcuate-shaped stops 1514 formed along the inner surface of the annular wall 1502. The valve housing 1500 is shown comprising disc-shaped construction, but in other embodiments, the construction of the valve housing 1500 may include other suitable geometric shapes. The valve housing 1500 and its components may be constructed from plastic, aluminum, stainless steel, or any other suitable material.

The diaphragm 1520 may comprise an extended arch-shaped body 1522 having a fixed end 1524 and a free end 1526. The diaphragm 1520 is preferably constructed from rubber, latex, polymers, or any other non-porous pliable material. In other embodiments, the diaphragm 1520 may be constructed from filtering media As shown, the diaphragm 1520 is configured to be assembled within an arch-shaped recess 1516 formed in the landing region 1504 of the valve housing 1500. When assembled within the recess 1516, the fixed portion 1524 of the diaphragm 1520 may be affixed to a seat portion 1517 of the recess 1516, while the free end 1526 may be configured to rest atop a rim portion 1518 of the recess 1516. In this way, when unrestricted, the free end 1526 of the diaphragm 1520 may be urged away from the rim portion 1518 of the recess 1516 under positive pressure to permit air to pass from the valve 1408 when the wearer exhales. But the free end 1526 is also configured such that it may be drawn toward the rim portion 1518 under negative pressure to create a seal between the free end 1526 and the rim portion 1518 that prevents air from passing into the valve 1408 when the wearer inhales.

The valve gate 1530 may include an elongated plate member 1532 having a top arc-shaped tab 1534, a bottom arc-shaped tab 1536, and a cut-out 1538 formed in the middle of the plate member 1532. The arc-shaped ends 1534 may be chamfered to define bearing surfaces 1533 that engage stops 1514. The valve gate 1530 may be assembled over the diaphragm 1520 to retain the diaphragm in the recess 1516 of the landing region 1504.

The valve cap indicator 1540 may comprise a thin-disc-shaped plate 1542 having indicia 1544 inscribed on its upper surface 1546. In the example shown, the indicia 1544 includes the wording "VENTED" and "CLOSED" to correspond to the two modes of operation of the respiratory valve 1408. The valve cap indicator 1540 may further include an outer periphery 1548 preferably constructed to diametrical dimensions that correspond to the diametrical dimensions of the inner diameter of the annular wall 1502 such that the outer periphery 1548 mates with an annular wall 1502 to enclose the cell 1506 of the valve housing 1500.

The valve cap indicator 1540 may be constructed from plastic, aluminum, stainless steel, or any other suitable material. The indicia 1544 may be inscribed or etched into the upper surface 1546 of the valve cap indicator 1540. In other embodiments, the indicia 1544 may include stickers, light-emitting diodes, or may be painted on the upper surface 1546 of the valve cap indicator 1540.

Respiratory valve 1408 may be operable in two modes of operation: a vented mode and closed mode. FIGS. 16A and 16B illustrate the respiratory valve 1408 in the vented mode.

In the vented mode, the top tab 1534 of the valve gate 1530 is engaged by the wearer to push the plate member 1532 downward such that the cut-out 1538 is positioned over the free end 1526 of the diaphragm 1520. The vertical translation of the valve gate 1530 is restricted by stops 1514. In this position, the free end 1526 of the diaphragm 1520 is unrestricted and may be urged away from the rim portion 1518 (FIG. 15) of the recess 1516 under positive pressure to permit air to pass from the valve 1408 when the wearer exhales, as shown by arrows 1602. Alternatively, the free end 1526 may be urged or drawn toward the rim portion 1518 (FIG. 15) under negative pressure to create a seal between the free end 1526 and the rim portion 1518 that prevents air from passing into the valve 1408 when the wearer inhales.

FIGS. 17A and 17B illustrate respiratory valve 1408 in the closed mode. In the closed mode, a bottom tab 1536 of the valve gate 1530 is engaged by the wearer to push the plate member 1532 upwards such that the plate member 1532 is positioned over the free end 1526 of the diaphragm 1520, thus abutting the free end 1526 against the rim portion 1518 (FIG. 15) of the recess 1516. The upward vertical translation of the valve gate 1530 is restricted by stops 1514. Because the free end 1526 is secured against the rim portion 1518 (FIG. 15), a seal is created between the free end 1526 and the rim portion 1518 (FIG. 15) 1120 air is prevented from flowing through the valve 1408 when the wearer inhales or exhales. Therefore, air will only pass through the filtering layers of the facemask 1402 when the wearer inhales and exhales, for optimum safety.

The present invention may be implemented in various embodiments, namely, manual, automatic, or a combination of manual and automatic. While the present invention depicts a screw mechanism to open and close the valve, there are many other potential methods that could be utilized. For example, instead of a screw, the hubs may be advanced and retracted along a rod utilizing a push or pull mechanism. In other embodiments, the hubs may be translated by other sliding or rotating mechanisms.

In some embodiments, the filtering facepiece respirator may also include smart bio-sensors that detect and measure intra-mask oxygen saturation levels, carbon dioxide levels, nucleic acid levels, the volume of expired or inspired air, as well as detect air leakage from the facemask. In these embodiments, the smart sensors may report data to a central processing unit, where the central processing unit uses the smart sensor data to alert the user of a change in mask environment conditions.

Other embodiments may be fitted with RF technology that provides communication between the respirator and a mobile device or central processing unit to control the respirator's mode of operation. In these embodiments, the controller may be integrated for use within public spaces such as offices, hospitals, clinics, restaurants, public and private buildings, service businesses, gyms and health clubs, and retailers.

In some embodiments, the entire respirator may be discarded. In other embodiments, the filtering layer material may be replaceable. In other embodiments, the respiratory valve may be replaceable while the facemask is preserved.

While the embodiments described in the present disclosure teach respiratory valves generally having annual-shaped construction, other respiratory valves and components according to the teachings of the present disclosure may include square-spaced, triangular-shaped, pentagon-shaped, or other geometrical-shaped constructions.

In general, terms such as "coupled to," and "configured for coupling to," and "secured to," and "configured for securing to" and "in communication with" (for example, a first component is "coupled to" or "is configured for coupling to" or is "configured for securing to" or is "in communication with" a second component) are used herein to indicate a structural, functional, mechanical, electrical, signal, optical, magnetic, electromagnetic, ionic or fluidic relationship between two or more components or elements. As such, the fact that one component is said to be in communication with a second component is not intended to exclude the possibility that additional components may be present between, and/or operatively associated or engaged with, the first and second components.

Although the previous description illustrates particular examples of various implementations, the present disclosure is not limited to the foregoing illustrative examples. A person skilled in the art is aware that the disclosure as defined by the appended claims and their equivalents can be applied in various further implementations and modifications. In particular, a combination of the various features of the described implementations is possible, as far as these features are not in contradiction with each other. Accordingly, the foregoing description of implementations has been presented for purposes of illustration and description. Modifications and variations are possible in light of the above description.

What is claimed is:

1. A filtering facepiece respirator comprising:
a facemask adapted to fit over the nose and mouth of a wearer, the facemask comprising a mask body containing a filtering structure;
a harness coupled to the mask body for securing the facemask on the face of the wearer; and
a mechanical valve coupled to a portion of the mask body proximate the wearer's mouth, the valve being manually adjustable between a first mode of operation and a second mode of operation, where in the first mode of operation air is permitted to flow through the valve on exhalation but not on inhalation and in the second mode of operation air is obstructed from flowing through the valve on exhalation and inhalation,
where the valve comprises a valve housing having an interior chamber, a fixed hub member disposed within the chamber, a first movable hub member disposed within the chamber, a pliable diaphragm disposed between the fixed hub member and the first movable hub member, a screw member disposed within the chamber extending along a longitudinal axis of the valve housing, and an adjustable dial, the adjustable dial being rotatable about the longitudinal axis, where the adjustable dial is coupled to the screw member and the screw member is threadedly coupled to the first movable hub member such that when the adjustable dial is rotated by the wearer, the screw member is also rotated and the threaded engagement between the screw member and the first movable hub member causes the first movable hub member to translate axially along the longitudinal axis away from or towards the fixed hub member.

2. The filtering facepiece respirator of claim 1, where the mask body comprises a first porous layer and a filtering layer.

3. The filtering facepiece respirator of claim 1, where the mask body comprises a first porous layer, a second porous layer, and a filtering layer, where the filtering layer is disposed between the first porous layer and the second porous layer.

4. The filtering facepiece respirator of claim 1, where in the first mode of operation the first movable hub member is spaced apart from the fixed hub member, thus permitting an outer periphery of the diaphragm to be urged away from the fixed hub member under positive pressure and air is allowed to freely flow through the valve when the wearer exhales.

5. The filtering facepiece respirator of claim 4, where the outer periphery of the diaphragm is drawn towards the fixed hub member under negative pressure to obstruct the flow of air through the valve when the wearer inhales.

6. The filtering facepiece respirator of claim 1, where in the second mode of operation the first movable hub member abuts the fixed hub member to secure the diaphragm therebetween, thus retaining an outer periphery of the diaphragm in contact with the fixed hub member to create a seal therebetween that obstruct air from flowing through the valve when the wearer exhales or inhales.

7. The filtering facepiece respirator of claim 1, where the valve may be adjusted to a third mode of operation, where in the third mode of operation air is permitted to flow through the valve when the wearer inhales or exhales.

8. The filtering facepiece respirator of claim 1, where the valve may be adjusted from one mode of operation to another mode of operation by a switch, slidable gate, rod, rotating arm, lever, button, toggle, dial, knob, joystick, rheostat, or electronic controller.

9. The filtering facepiece respirator of claim 1 further comprising a valve cap indicator coupled to a front portion of the valve housing, the valve cap indicator comprising a plate of material inscribed with indicia indicating the state of airflow through the valve utilizing a colored indicator, label, light indicator, auditory system, or display.

10. The filtering facepiece respirator of claim 1, where the diaphragm is made of a material that filters microscopic particulates.

* * * * *